(12) United States Patent  
Miles et al.

(10) Patent No.: US 8,690,911 B2  
(45) Date of Patent: Apr. 8, 2014

(54) MEDICAL DEVICE FOR MODIFICATION OF LEFT ATRIAL APPENDAGE AND RELATED SYSTEMS AND METHODS

(75) Inventors: Scott D. Miles, Sandy, UT (US); Brian K. Whisenant, Salt Lake City, UT (US); Daryl R. Edmiston, Draper, UT (US); Clark C. Davis, Holladay, UT (US)

(73) Assignee: Coherex Medical, Inc., Salt Lake City, UT (US)

( * ) Notice: Subject to any disclaimer, the term of this patent is extended or adjusted under 35 U.S.C. 154(b) by 272 days.

(21) Appl. No.: 12/684,764

(22) Filed: Jan. 8, 2010

(65) Prior Publication Data

US 2011/0022079 A1    Jan. 27, 2011

Related U.S. Application Data

(60) Provisional application No. 61/164,313, filed on Mar. 27, 2009, provisional application No. 61/160,247, filed on Mar. 13, 2009, provisional application No. 61/143,360, filed on Jan. 8, 2009.

(51) Int. Cl.  
*A61B 17/08* (2006.01)

(52) U.S. Cl.  
USPC .................. 606/213; 606/200; 606/139

(58) Field of Classification Search  
USPC .................. 606/151, 157, 158, 200, 213  
See application file for complete search history.

(56) References Cited

U.S. PATENT DOCUMENTS

| | | |
|---|---|---|
| 3,095,877 A | 7/1963 | Rowan |
| 3,874,388 A | 4/1975 | King et al. |
| 5,192,301 A | 3/1993 | Tamiya et al. |
| 5,284,488 A | 2/1994 | Sideris |
| 5,334,217 A | 8/1994 | Das |
| 5,425,733 A | 6/1995 | Schmieding |
| 5,425,740 A | 6/1995 | Hutchinson, Jr. |
| 5,433,727 A | 7/1995 | Sideris |
| 5,861,003 A | 1/1999 | Latson et al. |
| 5,904,703 A | 5/1999 | Gilson |
| 5,910,154 A | 6/1999 | Tsugita et al. |
| 6,152,144 A | 11/2000 | Lesh et al. |
| 6,174,322 B1 | 1/2001 | Schneidt |

(Continued)

FOREIGN PATENT DOCUMENTS

| | | |
|---|---|---|
| DE | 10 2006 056 283 | 6/2008 |
| EP | 1 266 630 | 12/2002 |

(Continued)

OTHER PUBLICATIONS

International Search Report dated Jun. 15, 2009, for International Application No. PCT/US2008/080374 (7 pages).

(Continued)

*Primary Examiner* — Corrine M McDermott  
*Assistant Examiner* — Alexander Orkin  
(74) *Attorney, Agent, or Firm* — Holland & Hart LLP

(57) ABSTRACT

A medical device, system and method for modifying a left atrial appendage ("LAA"). The medical device system includes a tether anchored within the LAA and one or more tissue growth members or occluders configured to be slid over the tether and lodged within the LAA. With this arrangement, a physician may close-off the LAA with a selective number of tissue growth members to meet the varying LAA sizes as determined from imaging information while conducting the procedure.

20 Claims, 17 Drawing Sheets

(56) References Cited

U.S. PATENT DOCUMENTS

| | | | |
|---|---|---|---|
| 6,231,561 B1 | 5/2001 | Frazier et al. | |
| 6,238,403 B1 | 5/2001 | Greene et al. | |
| 6,290,674 B1 | 9/2001 | Roue et al. | |
| 6,328,727 B1 | 12/2001 | Frazier et al. | |
| 6,355,051 B1 | 3/2002 | Sisskind et al. | |
| 6,371,971 B1 | 4/2002 | Tsugita et al. | |
| 6,419,669 B1 | 7/2002 | Frazier et al. | |
| 6,436,088 B2 | 8/2002 | Frazier et al. | |
| 6,458,100 B2 | 10/2002 | Roue et al. | |
| 6,488,689 B1 | 12/2002 | Kaplan et al. | |
| 6,530,934 B1 | 3/2003 | Jacobsen et al. | |
| 6,551,303 B1 | 4/2003 | Van Tassel et al. | |
| 6,551,341 B2 | 4/2003 | Boylan et al. | |
| 6,561,969 B2 | 5/2003 | Frazier et al. | |
| 6,641,557 B1 | 11/2003 | Frazier et al. | |
| 6,650,923 B1 | 11/2003 | Lesh et al. | |
| 6,652,555 B1 | 11/2003 | VanTassel et al. | |
| 6,652,556 B1 | 11/2003 | VanTassel et al. | |
| 6,666,861 B1 | 12/2003 | Grabek | |
| 6,689,150 B1 | 2/2004 | VanTassel et al. | |
| 6,702,825 B2 | 3/2004 | Frazier et al. | |
| 6,706,065 B2 | 3/2004 | Langberg et al. | |
| 6,712,804 B2 | 3/2004 | Roue et al. | |
| 6,730,108 B2 | 5/2004 | Van Tassel et al. | |
| 6,746,472 B2 | 6/2004 | Frazier et al. | |
| 6,790,229 B1 | 9/2004 | Berreklouw | |
| 6,949,113 B2 | 9/2005 | Van Tassel et al. | |
| 6,979,344 B2* | 12/2005 | Jones et al. | 606/200 |
| 6,994,092 B2 | 2/2006 | van der Burg et al. | |
| 7,011,671 B2 | 3/2006 | Welch | |
| 7,014,645 B2 | 3/2006 | Greene, Jr. et al. | |
| 7,025,756 B2 | 4/2006 | Frazier et al. | |
| 7,044,134 B2 | 5/2006 | Khairkhahan et al. | |
| 7,056,294 B2 | 6/2006 | Khairkhahan et al. | |
| 7,115,110 B2 | 10/2006 | Frazier et al. | |
| 7,128,073 B1 | 10/2006 | van der Burg et al. | |
| 7,152,605 B2 | 12/2006 | Khairkhahan et al. | |
| 7,169,164 B2 | 1/2007 | Borillo et al. | |
| 7,192,439 B2 | 3/2007 | Khairkhahan et al. | |
| 7,226,458 B2 | 6/2007 | Kaplan et al. | |
| 7,293,562 B2 | 11/2007 | Malecki et al. | |
| 7,597,704 B2 | 10/2009 | Frazier et al. | |
| 7,608,091 B2 | 10/2009 | Goldfarb et al. | |
| 7,717,937 B2 | 5/2010 | Wahr et al. | |
| 7,727,189 B2 | 6/2010 | Van Tassel et al. | |
| 7,780,645 B2 | 8/2010 | Jones | |
| 7,842,054 B2 | 11/2010 | Greene, Jr. et al. | |
| 8,142,470 B2* | 3/2012 | Quinn et al. | 606/194 |
| 2001/0003161 A1 | 6/2001 | Vardi et al. | |
| 2002/0026094 A1 | 2/2002 | Roth | |
| 2002/0026217 A1 | 2/2002 | Baker et al. | |
| 2002/0062130 A1* | 5/2002 | Jugenheimer et al. | 606/142 |
| 2002/0177855 A1 | 11/2002 | Greene, Jr. et al. | |
| 2002/0183787 A1* | 12/2002 | Wahr et al. | 606/213 |
| 2003/0014075 A1 | 1/2003 | Rosenbluth et al. | |
| 2003/0055455 A1 | 3/2003 | Yang et al. | |
| 2003/0057156 A1 | 3/2003 | Peterson et al. | |
| 2003/0120337 A1 | 6/2003 | Van Tassel et al. | |
| 2003/0125790 A1 | 7/2003 | Fastovsky et al. | |
| 2003/0171739 A1 | 9/2003 | Murphy et al. | |
| 2003/0181942 A1 | 9/2003 | Sutton et al. | |
| 2003/0187474 A1 | 10/2003 | Keegan et al. | |
| 2003/0191526 A1 | 10/2003 | Van Tassel et al. | |
| 2003/0195555 A1 | 10/2003 | Khairkhahan et al. | |
| 2003/0199923 A1 | 10/2003 | Khairkhahan et al. | |
| 2003/0204203 A1 | 10/2003 | Khairkhahan et al. | |
| 2003/0212432 A1 | 11/2003 | Khairkhahan et al. | |
| 2003/0220667 A1 | 11/2003 | van der Burg et al. | |
| 2004/0034366 A1 | 2/2004 | Van Der Burg et al. | |
| 2004/0122467 A1 | 6/2004 | VanTassel et al. | |
| 2004/0127935 A1 | 7/2004 | VanTassel et al. | |
| 2004/0215230 A1 | 10/2004 | Frazier et al. | |
| 2004/0260317 A1 | 12/2004 | Bloom et al. | |
| 2004/0267191 A1 | 12/2004 | Gifford, III et al. | |
| 2005/0004652 A1 | 1/2005 | van der Burg et al. | |
| 2005/0033409 A1 | 2/2005 | Burke et al. | |
| 2005/0043759 A1 | 2/2005 | Chanduszko | |
| 2005/0049573 A1 | 3/2005 | Van Tassel et al. | |
| 2005/0060017 A1 | 3/2005 | Fischell et al. | |
| 2005/0065589 A1 | 3/2005 | Schneider et al. | |
| 2005/0075665 A1 | 4/2005 | Brenzel et al. | |
| 2005/0090860 A1* | 4/2005 | Paprocki | 606/213 |
| 2005/0113861 A1 | 5/2005 | Corcoran et al. | |
| 2005/0192616 A1 | 9/2005 | Callister et al. | |
| 2005/0192627 A1 | 9/2005 | Whisenant et al. | |
| 2005/0234540 A1 | 10/2005 | Peavey et al. | |
| 2005/0234543 A1 | 10/2005 | Glaser et al. | |
| 2005/0256532 A1 | 11/2005 | Nayak et al. | |
| 2005/0267524 A1 | 12/2005 | Chanduszko | |
| 2006/0009798 A1 | 1/2006 | Callister | |
| 2006/0009800 A1 | 1/2006 | Christianson et al. | |
| 2006/0036282 A1 | 2/2006 | Wahr et al. | |
| 2006/0052816 A1 | 3/2006 | Bates et al. | |
| 2006/0122646 A1 | 6/2006 | Corcoran et al. | |
| 2006/0149299 A1 | 7/2006 | Greene et al. | |
| 2006/0149307 A1 | 7/2006 | Durgin | |
| 2006/0149314 A1 | 7/2006 | Borillo et al. | |
| 2006/0206148 A1 | 9/2006 | Khairkhahan et al. | |
| 2006/0217761 A1* | 9/2006 | Opolski | 606/213 |
| 2006/0276839 A1 | 12/2006 | McGuckin, Jr. | |
| 2007/0083230 A1 | 4/2007 | Javois | |
| 2007/0083232 A1* | 4/2007 | Lee | 606/213 |
| 2007/0088388 A1 | 4/2007 | Opolski et al. | |
| 2007/0112382 A1 | 5/2007 | Thill et al. | |
| 2007/0123934 A1 | 5/2007 | Whisenant et al. | |
| 2007/0129757 A1* | 6/2007 | Armstrong | 606/213 |
| 2007/0173885 A1 | 7/2007 | Cartier et al. | |
| 2007/0179527 A1 | 8/2007 | Eskuri et al. | |
| 2007/0179583 A1 | 8/2007 | Goetzinger et al. | |
| 2007/0191884 A1 | 8/2007 | Eskridge et al. | |
| 2007/0198059 A1* | 8/2007 | Patel et al. | 606/213 |
| 2007/0237720 A1 | 10/2007 | Padilla et al. | |
| 2007/0276415 A1* | 11/2007 | Kladakis et al. | 606/151 |
| 2008/0039929 A1 | 2/2008 | Davis et al. | |
| 2008/0119891 A1 | 5/2008 | Miles et al. | |
| 2008/0215086 A1* | 9/2008 | Olsen et al. | 606/213 |
| 2009/0025820 A1 | 1/2009 | Adams | |
| 2009/0069840 A1 | 3/2009 | Hallisey | |
| 2009/0099596 A1 | 4/2009 | McGuckin, Jr. et al. | |
| 2009/0112249 A1 | 4/2009 | Miles et al. | |
| 2009/0318948 A1 | 12/2009 | Linder et al. | |
| 2010/0228279 A1 | 9/2010 | Miles et al. | |
| 2010/0228285 A1 | 9/2010 | Miles et al. | |
| 2010/0234878 A1 | 9/2010 | Hruska et al. | |
| 2010/0324585 A1 | 12/2010 | Miles et al. | |
| 2010/0324586 A1 | 12/2010 | Miles et al. | |
| 2010/0324587 A1 | 12/2010 | Miles et al. | |
| 2010/0324588 A1 | 12/2010 | Miles et al. | |
| 2011/0046658 A1 | 2/2011 | Connor et al. | |
| 2011/0054515 A1 | 3/2011 | Bridgeman et al. | |
| 2011/0208233 A1 | 8/2011 | McGuckin, Jr. et al. | |
| 2012/0316584 A1 | 12/2012 | Miles et al. | |

FOREIGN PATENT DOCUMENTS

| | | |
|---|---|---|
| EP | 1 358 850 | 11/2003 |
| EP | 1 523 957 | 4/2005 |
| EP | 1 741 393 | 1/2007 |
| WO | 99/33402 | 7/1999 |
| WO | 00/27292 | 5/2000 |
| WO | 01/93920 | 12/2001 |
| WO | 02/071977 | 9/2002 |
| WO | 03/028802 | 4/2003 |
| WO | 2004045393 A2 | 6/2004 |
| WO | 2005053547 | 6/2005 |
| WO | 2005099365 | 10/2005 |
| WO | 2006033641 | 3/2006 |
| WO | 2006047748 A2 | 5/2006 |
| WO | 2007054116 | 5/2007 |

(56) References Cited

FOREIGN PATENT DOCUMENTS

| WO | 2010081033 A1 | 7/2010 |
| WO | 2010148246 A2 | 12/2010 |

OTHER PUBLICATIONS

U.S. Appl. No. 12/684,783, filed Jan. 8, 2010, entitled "Medical Device for Modfication of Left Atrial Appendage and Related Systems and Methods."

U.S. Appl. No. 12/684,795, filed Jan. 8, 2010, entitled "Medical Device for Modfication of Left Atrial Appendage and Related Systems and Methods."

International Search Report dated May 6, 2010, for International Application No. PCT/US2010/020539 (5 pages).

International Search Report dated May 7, 2010, for International Application No. PCT/US2010/020547 (4 pages).

International Search Report dated Apr. 26, 2010, for International Application No. PCT/US2010/020549 (7 pages).

* cited by examiner

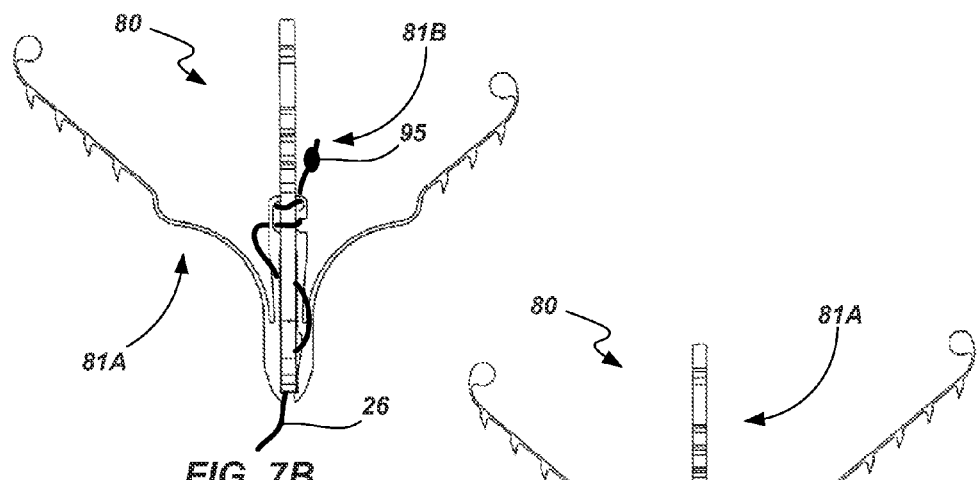
FIG. 7B
FIG. 7C
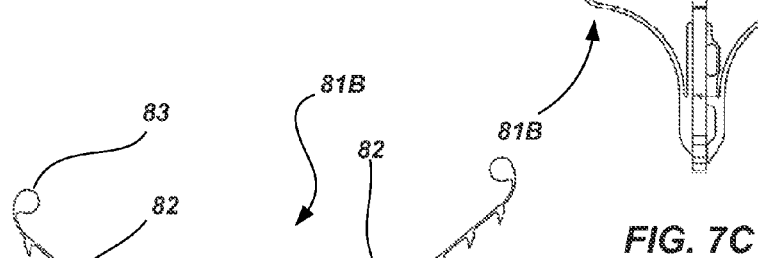
FIG. 7D
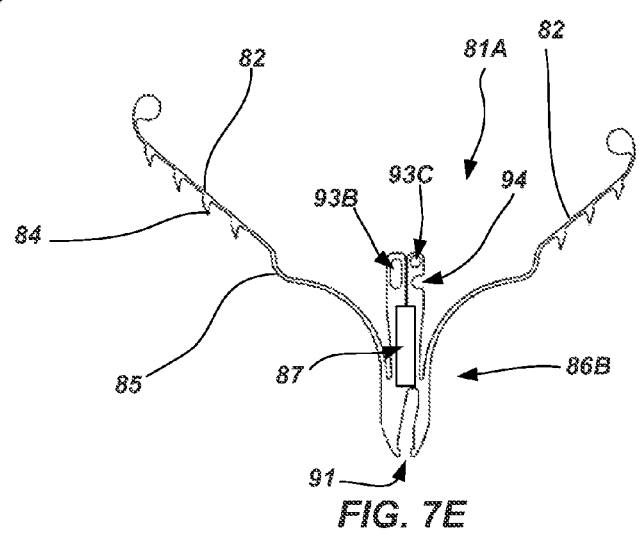
FIG. 7E

MEDICAL DEVICE FOR MODIFICATION OF LEFT ATRIAL APPENDAGE AND RELATED SYSTEMS AND METHODS

CROSS-REFERENCE TO RELATED APPLICATIONS

This application claims the benefit of U.S. Provisional Patent Application No. 61/143,360, filed Jan. 8, 2009, entitled MEDICAL DEVICE FOR MODIFICATION OF LEFT ATRIAL APPENDAGE AND RELATED SYSTEMS AND METHODS, and of U.S. Provisional Patent Application No. 61/160,247, filed Mar. 13, 2009, entitled MEDICAL DEVICE FOR MODIFICATION OF LEFT ATRIAL APPENDAGE AND RELATED SYSTEMS AND METHODS, and of U.S. Provisional Patent Application No. 61/164,313, filed Mar. 27, 2009, entitled MEDICAL DEVICE FOR MODIFICATION OF LEFT ATRIAL APPENDAGE AND RELATED SYSTEMS AND METHODS, the disclosure of each of which are incorporated by reference herein in their entireties.

TECHNICAL FIELD

The present invention relates generally to the modification of an atrial appendage and, more specifically, to devices, systems and methods for occluding or otherwise structurally altering such appendages.

BACKGROUND

The atrial appendage is a feature of all human hearts. The upper chambers of the heart, the atria, have this appendage attached to each of them. The physiologic function of such appendages is not completely understood, but they do act as a filling reservoir during the normal pumping of the heart. The appendages typically protrude from the atria and cover an external portion of the atria. Atrial appendages differ substantially from one to another in size, shape and specific location with respect to the atria. For example, one atrial appendage may be configured as a tapered protrusion while another atrial appendage may be configured as axe-entrant, sock-like hole. The inner surface of an appendage is conventionally trabeculated with cords of muscular cardiac tissue traversing its surface with one or more lobes.

The atrial appendages are inert while blood is being pumped through them during normal heart function. In other words, the appendages don't have a noticeable effect on blood pumped through them during normal heart function. However, in cases of atrial fibrillation, when the atria go into arrhythmia, blood may pool and thrombose inside of the appendages. Among other things, this can pose a stroke risk when it occurs in the left appendage since the thrombus may be pumped out of the heart and into the cranial circulation. Such can also lead to ischemic damage of other organs of the body.

Historically, atrial appendages have sometimes been modified surgically to reduce the risk imposed by atrial fibrillation. In more recent years, devices which may be delivered percutaneously into the left atrial appendage have been introduced. The basic function of these devices is to exclude the volume within the appendage with an implant which then allows blood within the appendage to safely thrombose and then to be gradually incorporated into cardiac tissue. This can leave a smooth, endothelialized surface where the appendage used to be.

In comparison to surgical procedures, devices implanted percutaneously are clearly a less invasive means for addressing the problems associated with the left atrial appendage. However, due to the wide variability of the size of the ostium and the volume of an atrial appendage, implant devices that are currently used typically include structure that cannot meet such variability, resulting in inadequate devices for many left atrial appendages. Further, such implant devices are substantially limited by the orientation by which they can successfully be deployed. Thus, successful placement and deployment of such devices becomes limited.

As such, it would be advantageous to provide percutaneous systems, methods and devices that, among other things, address one or more issues such as implant orientation and the variability in sizes of the left atrial appendage in order to provide high success in left atrial appendage modification.

BRIEF SUMMARY

The present invention includes various embodiments of medical devices, systems and methods for modifying an atrial appendage. In accordance with one embodiment, a medical device system for modifying a left atrial appendage is provided. The system includes a catheter having a lumen extending therethrough. A tether extends through the lumen of the catheter and an anchoring member is coupled with the tether. At least one tissue growth member is slidably coupled with the tether and sized and configured to be positioned within the left atrial appendage. A locking element is associated with the at least one tissue growth member and the tether.

In one embodiment, the tissue growth member may include a foam material. In certain embodiments the at least one tissue growth member may include a plurality of tissue growth members which are similarly or differently configured as compared to each other. The system may include a pusher member configured to advance the at least one tissue growth member through the catheter. Various other embodiments may provide anchors of various configuration, use of different deployment mechanisms, and tissue growth members or occluders of various configurations.

In accordance with another embodiment of the present invention, a method for modifying a left atrial appendage is provided. The method includes positioning a catheter adjacent the left atrial appendage. A tether is anchored within the left atrial appendage and at least one tissue growth member is slid over the tether. The at least one tissue growth member is deployed within the left atrial appendage and maintained therein with a locking element.

The method may further include, as part of anchoring the tether, positioning the catheter having an anchoring member in a constrained configuration within the catheter relative to the left atrial appendage, and deploying the anchoring member in an expanded configuration to anchor the anchoring member in the left atrial appendage.

In one embodiment, the method may further include deploying the at least one tissue growth member within a first lobe of the left atrial appendage and wherein the method further comprises deploying at least one other tissue growth member in a second lobe of the left atrial appendage.

BRIEF DESCRIPTION OF THE SEVERAL VIEWS OF THE DRAWINGS

The foregoing and other advantages of various embodiments of the invention will become apparent upon reading the following detailed description and upon reference to the drawings in which:

FIGS. 7A through 7E are various views of components that may be used in one or more embodiments of the present invention;

DETAILED DESCRIPTION OF THE INVENTION

Figure 1:
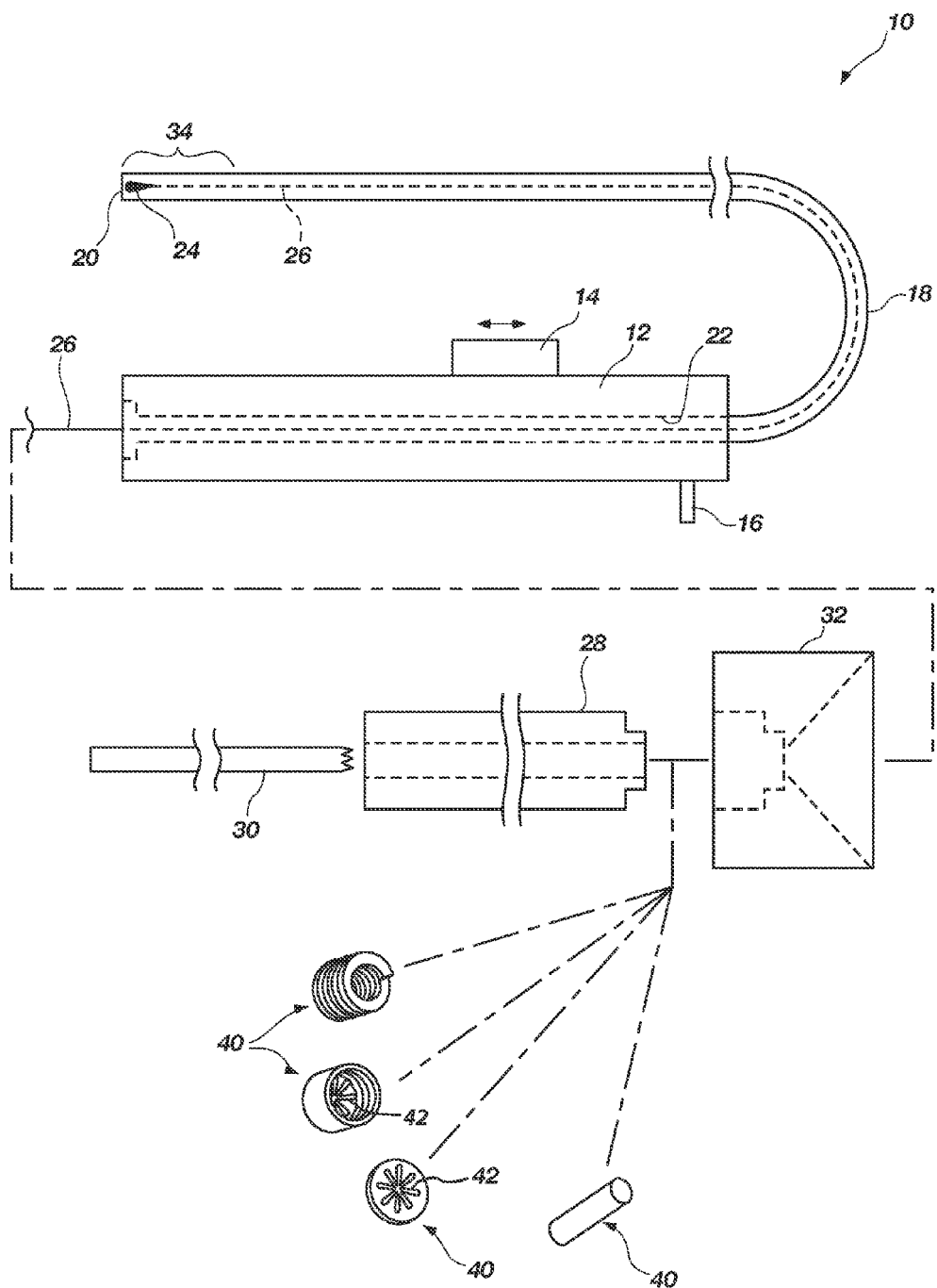
FIG. 1 is an exploded view of various components of a medical device system, according to an embodiment of the present invention.

Referring to FIG. 1, a medical device system 10 is shown that may be used to occlude or modify an opening or cavity such as, for example, a left atrial appendage (LAA). In one embodiment, the medical device system 10 may include a handle 12 with an actuator 14 and fluid port 16. The fluid port 16 may be used to flush out the catheter when in use as will be appreciated by those of ordinary skill in the art. In addition, the system 10 includes a catheter 18 with a catheter lumen 20 extending longitudinally therethrough and attached to a distal end of the handle 12. The catheter lumen 20 may coincide and communicate with a handle lumen 22 as well as communicate with the fluid port 16. The actuator 14 may be configured to actuate or move the catheter 18 proximally and distally, relative to an associated tether 26, to deploy and capture, respectively, an anchoring member 24 disposed at a distal end of the tether 26. The tether 26 may be configured to extend through and be positioned within the catheter lumen 20. The tether 26 may also extend through the handle lumen 22 and may extend out of a proximal end of the handle 12.

The medical device system 10 may also include a capturing member 28, a pusher member 30 and a loading member 32 (which, in one example, as shown, may be configured as a funnel structure or device) may be for loading a tissue growth member 40 into the handle 12. As will be discussed in further detail below, the tissue growth member 40 may be displaced through the handle 12 and over the tether 26 to a distal portion 34 of the catheter 18 for deployment during a desired procedure to modify an atrial appendage. As depicted in FIG. 1, the tissue growth member 40 may exhibit various sizes and shapes. For example, the tissue growth member 40 may exhibit a shape similar to a cup, a disk, a cylinder, a coil configuration, or any other suitable shape or configuration, such as a spherical or semispherical geometry or the like. Such tissue growth members may also include a support structure 42 extending internally or externally (or both) of the tissue growth member 40. The tissue growth member 40 may be configured to be constrained and confined within the narrow configuration of a catheter 18 and, when released from the catheter, self expand to a larger configuration. The support structure 42 may be configured to assist the tissue growth member 40 to expand to its intended larger configuration as well as configured to assist the tissue growth member to be predictably captured within the capturing member 28 and pushed distally through the handle 12 and catheter 18. Such support structure 42 may be formed, for example, from a shape-memory alloy, such as a nickel-titanium alloy (also referred to as Nitinol), from a polymeric material or any other suitable flexible material known in the art.

According to one aspect of the present invention, the tissue growth member 40 may be a self expanding porous member, such as a polymer based foam or a polyurethane foam. Other materials with desired porosity may also be used, such as, for example, felt, fabric, a polyester fiber such as polyethylene terephthalate (PET, also known commercially as Dacron®), Nitinol braded wire, or Nitinol felt. In the case of foam, such foam may be a reticulated foam, typically undergoing a chemical or heating process to open the pours within the foam as known in the art. The foam may also be a non-reticulated foam. The foam may also include graded density and graded porosity, as desired, and manipulated to expand in a desired geometry when the support structure 42 is moved to the expanded configuration. The tissue growth member 40 is configured to induce tissue in-growth therethrough to, thereby, close the LAA opening. Further, the tether 26 may be formed from a metal or polymer based material or any other material suitable for maintaining access to the LAA with the anchor and to facilitate interconnection for one or more tissue growth members.

Figure 1A:
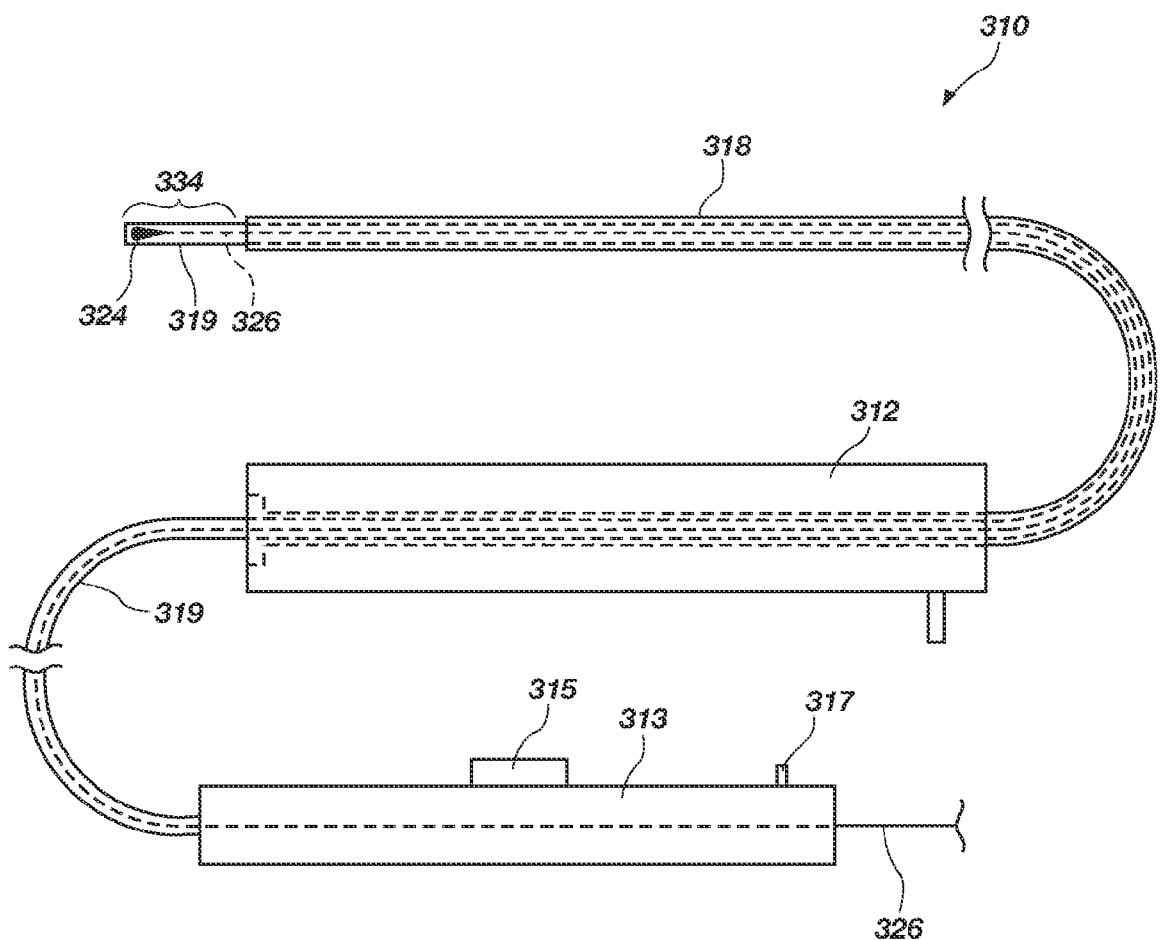
FIG. 1A is another embodiment of various components of a medical device system, according to the present invention.

FIG. 1A is another embodiment of a medical device system 310 with an additional component as compared to the embodiment shown in FIG. 1. The system 310 includes an anchor catheter 319 having an anchor catheter handle 313 with an actuator 315 and fluid port 317. The anchor catheter 319 also includes an anchor 324 and tether 326 combination, similar to that previously described, disposed within the anchor catheter 319. As such, the medical device system 310 includes a primary catheter 318 with a handle 312 and the anchor catheter 319 having the anchor catheter handle 313. Although only one anchor catheter 319 is depicted, there may be one or more anchor catheters in the system 330, depending on the number of tethers needed to be anchored within a particular atrial appendage. Further, the medical device system 310 of this embodiment also may include a elements shown in FIG. 1 such as a capturing member 28, loading member 32 and pusher member 30 to facilitate sliding the tissue growth member 40 in the handle 312 and through the primary catheter 318 of this embodiment.

Referring still to FIG. 1A, the anchor catheter 319 includes an anchor 324 positioned at a distal portion 334 of the anchor catheter 319 and a tether 326 coupled to, and extending from, the anchor 324. As in the previous embodiment, the tether 326 may extend through the anchor catheter 319 and the anchor catheter handle 313. Such anchor catheter 319 is sized and configured to be advanced through the handle 312 and the primary catheter 318 (or rather through associated lumens of the handle 312 and the primary catheter 318) for deploying the anchor 324 within the LAA. Likewise, the primary catheter 318 is sized and configured to receive the anchor catheter 319 through the handle 312 to be advanced distally through the primary catheter 318. With this arrangement, the primary catheter 318 may first be employed by advancing the primary catheter 318 through the right atrium, through the atrial septum wall via a septal puncture to enter the left atrium and navigated adjacent the LAA, utilizing standard catheterization techniques, as known to one of ordinary skill in the art. The anchor catheter 319 may then be advanced in the primary catheter 318 and, further, advanced beyond the primary catheter 318 and within the LAA. The anchor 324 may then be deployed via the actuator 315 and anchored within the LAA. The anchor catheter 319 may then be withdrawn from the LAA and from the primary catheter 318, leaving the tether 326 attached to the anchor 324 and extending through the primary catheter 318 while maintaining the primary catheter adjacent the LAA. The tissue growth member 40 (FIG. 1) may then be positioned over the tether 326 and advanced in the handle 312, similar to, for example, the embodiment disclosed in more detail below with respect to FIGS. 2A-2C.

Figure 2A:
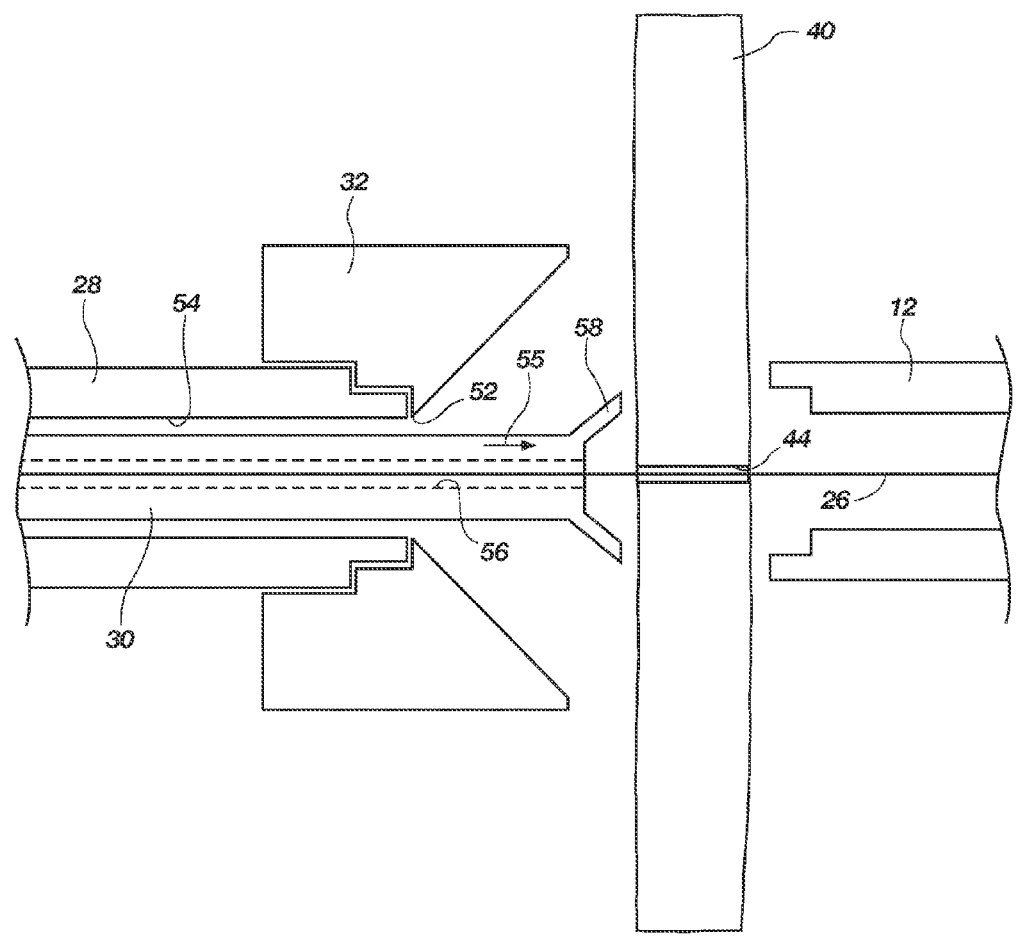
FIGS. 2A, 2B and 2C are cross-sectional views of a loading mechanism for loading a tissue growth member into a handle of the medical device system, according to one embodiment of the present invention.
Figure 2B:
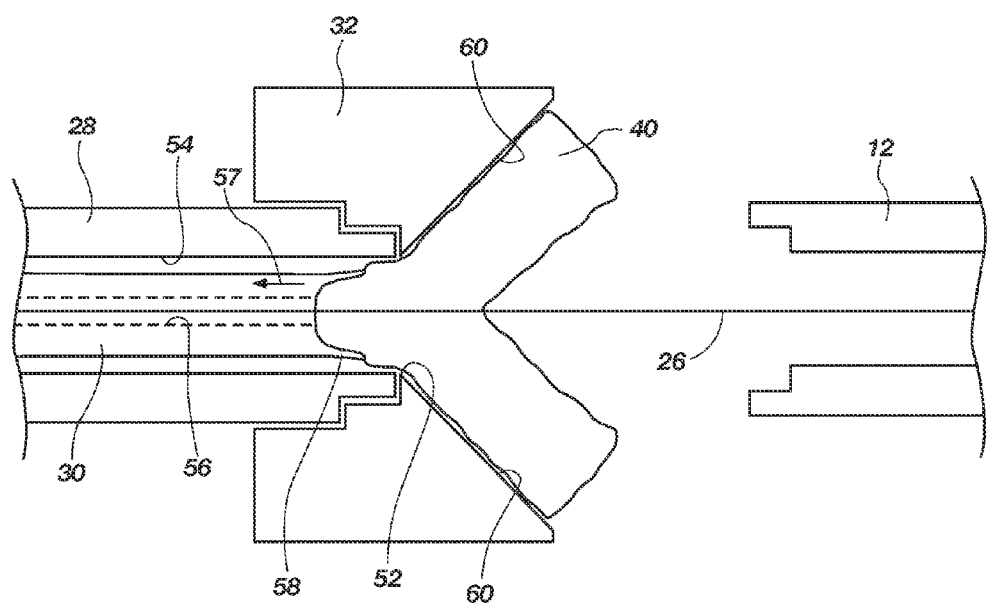
Figure 2C:
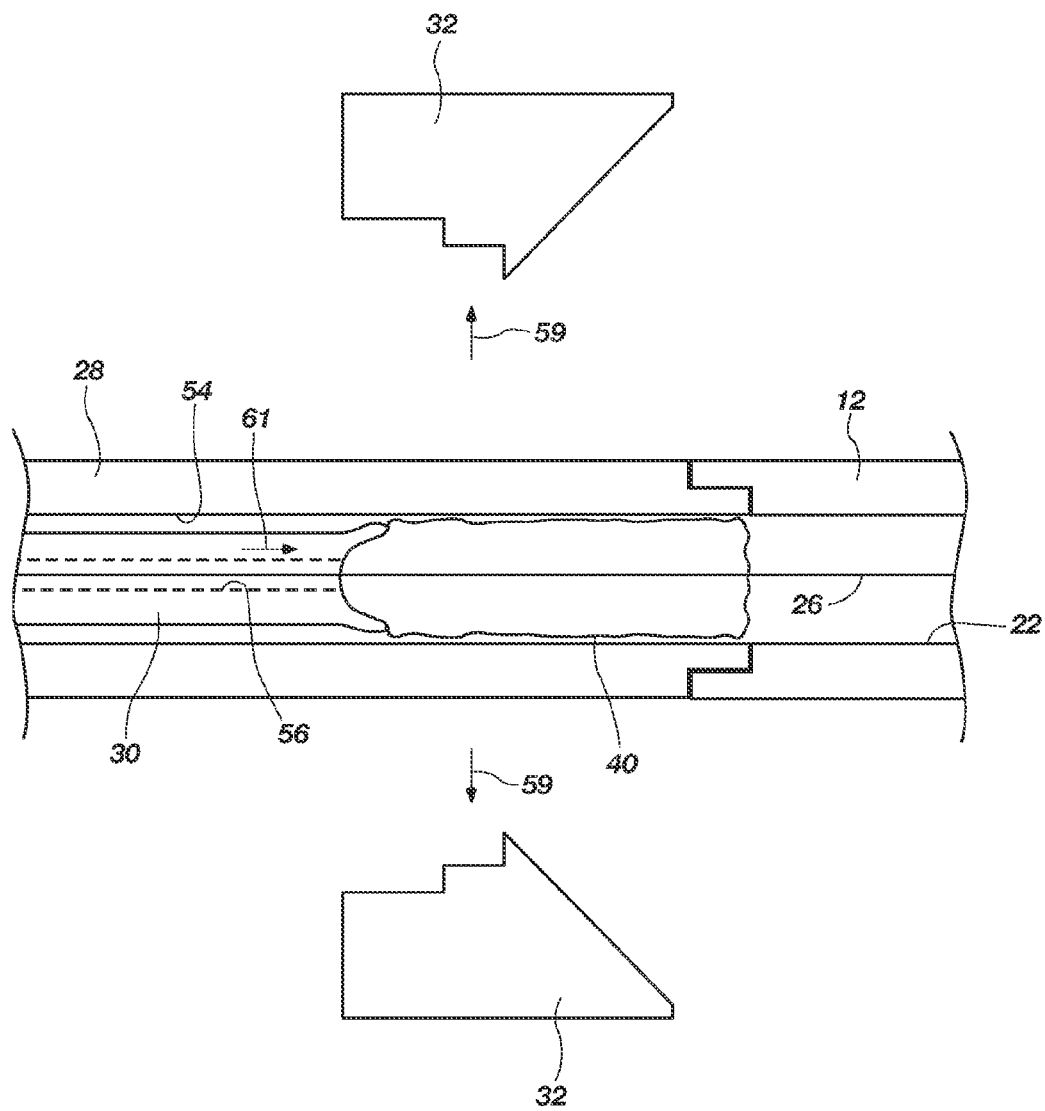

FIGS. 2A through 2C illustrate one method for loading the tissue growth member 40 into the handle 12 utilizing the capturing member 28, the loading member 32 and pusher member 30. For example, an opening 44 defined in the tissue growth member 40 may be configured such that the tether 26 passes therethrough. In one embodiment, the opening 44 may be defined centrally within the tissue growth member 40. The tether 26 may also be positioned through respective central bores 52, 54, 56 defined in each of the loading member 32, capturing member 28 and pusher member 30. As depicted in FIG. 2A, the pusher member 30 may be displaced distally through the capturing member 28 and loading member 32 and the loading member 32 may be attached to the distal end of the capturing member 28. The pusher member 30 may include a grasping portion 58 configured to grasp the tissue growth member 40. In one embodiment, the grasping portion 58 gabs or attaches to a portion of exposed support structure 42 (see FIG. 1) that, for example, extends through the tissue growth member 40 at a location adjacent the opening 44 of the tissue growth member 40. With this arrangement, the pusher member 30 may be moved distally, as indicated by arrow 55, to grab the tissue growth member 40.

As shown in FIG. 2B, the pusher member 30 may then be displaced proximally, as indicated by arrow 57, to pull the tissue growth member 40 against a surface 60 of the loading member 32 to assist the tissue growth member 40 to collapse or be compacted in a constricted and confined configuration and into the capturing member 28. As shown in FIG. 2C, once the tissue growth member 40 is constricted or contained within the capturing member 28, the loading member 32 may be removed from the capturing member 28, such as indicated by arrows 59. The tissue growth member 40 may then be moved distally, as indicated by arrow 61, into the handle 12 (or, more specifically, the handle lumen 22) via the pusher member 30 which may continue to push the tissue growth member 40 distally to a distal portion of the catheter (not shown). It is also contemplated that once the tissue growth member 40 is contained within the capturing member 28, the tissue growth member 40 may be moved to the distal portion of the catheter by other means. For example, the tissue growth member 40 may be displaced hydraulically such as by pushing saline through a fluid port to displace the tissue growth member distally. Further, it is contemplated that in another embodiment, the tissue growth member 40 may be loaded directly into the handle 12. In another embodiment, the tissue growth member 40 may be loaded or pre-loaded into a separate catheter and advanced distally over the tether 26, through the handle 12 and catheter 18, similar to that disclosed with respect to the anchor catheter 319 (see FIG. 1A).

Figure 3A:
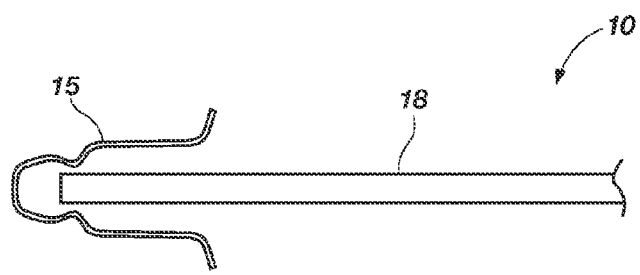
FIGS. 3A through 3D are cross-sectional views of respective steps utilizing the medical device system for modifying a left atrial appendage utilizing the medical device system, according to another embodiment of the present invention.
Figure 3B:
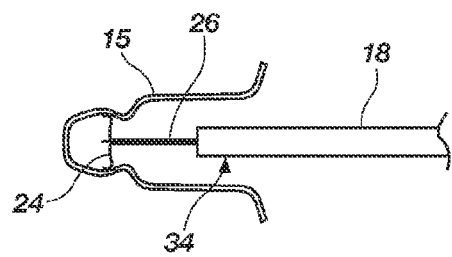

Referring now to FIGS. 3A through 3D, use of a medical device system 10 for modifying a left atrial appendage 15 is shown according to an embodiment of the present invention. As shown in FIG. 3A, the catheter 18 of the medical device system 10 is advanced to the left atrial appendage 15 of the heart. Such may be accomplished, for example, by advancing the catheter 18 through the septum wall of the heart via a trans-septal puncture. Imaging techniques, as known in the art, may be utilized for preferred positioning of the catheter 18 by advancing, for example, contrast through the catheter and into the left atrial appendage 15. Once a desired position of the catheter 18 is established, the catheter 18 may be moved proximally, via the actuator 14 (FIG. 1), to deploy an anchoring member 24 from a distal portion 34 of the catheter 18, as depicted in FIG. 3B. The anchoring member 24 is sized and configured to self expand and lodge within the left atrial appendage 15 such as by pressing and engaging against and with the walls of the left atrial appendage 15. The anchoring member 24 is configured to readily engage with the trabeculated tissue deep within the LAA. The physician or operator may pull on the tether 26, which is attached to the anchoring member 24, to ensure that the anchoring member 24 is sufficiently lodged within the left atrial appendage. If the anchoring member 24 becomes dislodged, the anchoring member 24 may be readily re-sheathed into the catheter 18 and another attempt may be made to position and lodge the anchoring member 24 within the left atrial appendage 15. It is noted that the tether 26 extends from a proximal end of the anchoring member 24 and through the catheter 18. Thus, the anchoring member 24 and tether 26 combination allow the physician to maintain catheter access to the left atrial appendage.

Figure 3C:
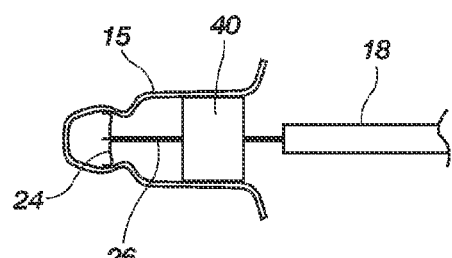
Figure 3D:
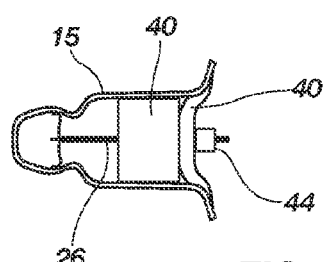

As depicted in FIG. 3C, a tissue growth member 40 is slid over the tether 26 through the catheter 18 and deployed in a desired position within the left atrial appendage 15. As previously set forth, the tissue growth member 40 may be loaded over the tether 26, as shown in FIGS. 2A through 2C, utilizing, for example, the catheter systems depicted in either FIG. 1 or 1A, or any other suitable method for delivering the tissue growth member 40, such as previously set forth. At this juncture, the physician may continue and utilize imaging techniques to determine if the tissue growth member 40 has sufficiently provided a surface that will substantially prevent thrombus from migrating from the left atrial appendage 15. If needed, depending on the wide breadth of variations of left atrial appendages, the physician may release one or more additional tissue growth members 40, as depicted in FIG. 3D. Once the physician is satisfied with the procedure, a locking element 44 may be slid over the tether 26 adjacent the proximal most tissue growth member 40, after which the tether 26 may be cut or otherwise terminated proximally of such locking element 44. The locking element 44 may be a clamp slid up the tether or a knot formed in the tether or any other suitable fixture configured to ensure the tissue growth element 40 does not migrate from its deployed position.

It should be noted that the medical device system of the present invention may include differently sized or shaped tissue growth members 40 so that a physician can utilize the size and shape necessary and best suited to create a surface that will substantially prevent thrombus from migrating from the left atrial appendage 15. In this manner, the physician can obtain imaging information while conducting the procedure and determine if proper occlusion of the LAA has been obtained and, if not, continue to determine and selectively choose appropriately sized additional tissue growth members to slide into the left atrial appendage to, thereby, occlude virtually any size or other variation that may be encountered when conducting such a procedure. Furthermore, it is noted that once the anchor 24 is lodged within the LAA for sliding one or more of the tissue growth members 40 over the tether 26 and into the LAA 15, any potential issues of device orientation are substantially eliminated as the tether provides a guide into the LAA 15 for placement of the tissue growth members 40.

Figure 4A:
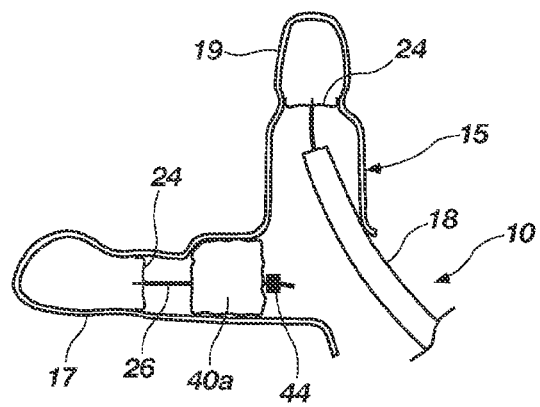
FIGS. 4A through 4C are cross-sectional views of respective steps utilizing the medical device system for modifying a left atrial appendage having a plurality of appendage lobes, according to another embodiment of the present invention.
Figure 4B:
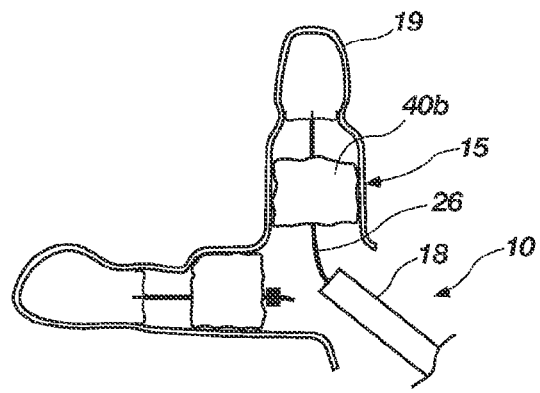
Figure 4C:
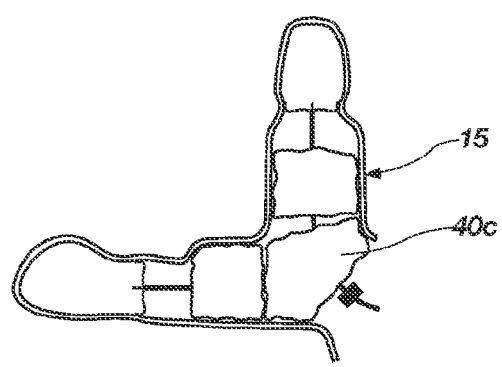

Referring now to FIGS. 4A through 4C, another method for employing the medical device system 10 of the present invention is provided wherein there are multiple lobes in the left atrial appendage 15. As depicted in FIG. 4A, a first tissue growth member 40a is positioned in a first lobe 17 of the left atrial appendage 15 by being slid over a tether 26 the tether 26 being held in place with the anchoring member 24 in the first lobe 17 (such as described with respect to FIGS. 3A-3C above), and the first tissue growth member 40a being prevented from migrating via the locking element 44 locked on the tether 26 at the proximal side of the first tissue growth member 40a. Another catheter 18 may then be advanced to deploy the anchoring member 24 in a second lobe 19 in the left atrial appendage 15 to anchor therein. As depicted in FIG. 4B, a second tissue growth member 40b may then be selectively chosen and deployed in the second lobe 19 with the tether 26 maintaining access to preferred positioning within the left atrial appendage 15 via its attachment to the anchor member 24 that has been deployed within the second lobe 19. As previously set forth, positioning the tissue growth member 40 in the LAA 15, in each instance, may include the step of loading the tissue growth member 40 over the tether 26 after the step of lodging the anchoring member 24 in the LAA 15 with the tether 26 extending therefrom. In some embodiments, deployment of individual tissue growth members 40a and 40b may be sufficient for occlusion or modification of the LAA 15. However, in other situations, deployment of additional tissue growth members may be desired or even required.

For example, as depicted in FIG. 4C, a third tissue growth member 40c may be selectively chosen and deployed so as to be sized and configured to best fit within the remaining space and effectively provide a surface that will substantially prevent thrombus from migrating from the left atrial appendage. Although the tissue growth members, due to the self expanding characteristics thereof, effectively lodge themselves within the left atrial appendage 15, to ensure such tissue growth members do not migrate from the left atrial appendage, the locking element 44 can be slid over the tether 26 and clamped to the tether 26 adjacent to the proximal side of the third tissue growth member 40c. In this manner, a left atrial appendage 15 with multiple lobes (e.g., 17 and 19) may be occluded to substantially prevent emboli from migrating from the left atrial appendage 15 and, over time, the tissue growth members will induce tissue in-growth therein to permanently create a tissue seal within the left atrial appendage 15.

As will be readily understood by one of ordinary skill in the art, instead of the catheter 18 employed in the embodiments disclosed with respect to FIGS. 3A through 3D and FIGS. 4A through 4C, the anchor catheter 319 may be employed with the primary catheter 318 as set forth and described with respect to FIG. 1A.

Figure 5:
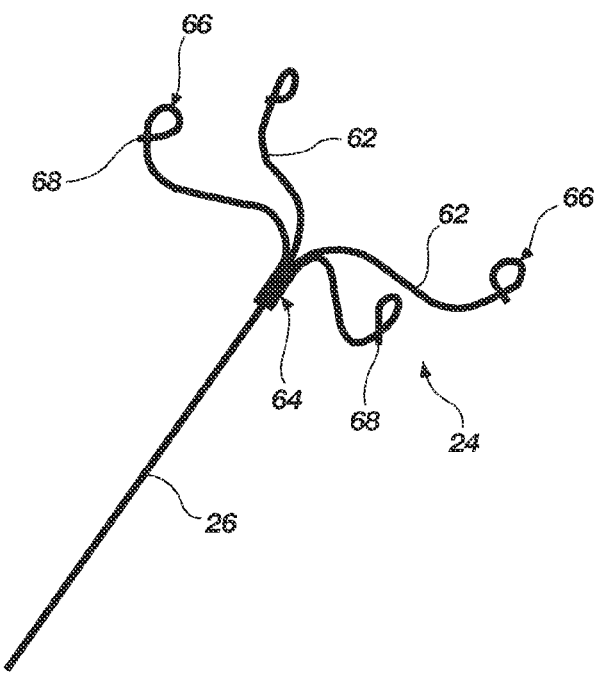
FIG. 5 is a perspective view of an anchoring member at a distal end of a tether, according to one embodiment of the present invention.

FIG. 5 depicts an anchoring member 24 interconnected to a distal end of the tether 26 according to one embodiment. Such an anchoring member 24 is sized and configured to be collapsed in a constrained configuration at the distal portion of the catheter (see FIG. 1). As previously set forth, once such anchoring member 24 is deployed from the catheter, the anchoring member 24 may self expand to an expanded or deployed configuration, as shown. The anchoring member 24 may include multiple legs 62 extending from a center portion 64, the center portion being interconnected to the tether 26. In the embodiment depicted in FIG. 5, there are four legs 62 extending from the center portion 64, however, in other embodiments there may be any suitable number of legs. Each leg 62 may extend radially outward and include a looped portion 66 at the radial outermost end thereof. Such looped portion 66 extends distally and then returns both radially inwardly and proximally such that a distal leg end 68 extends beyond a more proximal portion of the leg so as to act as an engagement nub to engage with the trabeculated tissue within the LAA. In this manner, the legs are sized and configured to extend within the left atrial appendage and anchor within such tissue. The looped portion 66 and the outward extending legs 62 may provide a spring effect to allow the physician to pull on the tether 26 without damaging the tissue when determining if the anchoring member 24 is sufficiently lodged within the left atrial appendage.

It is noted that a variety of other configurations may be employed for the anchoring member 24. For example, a variety of anchoring structures are disclosed in U.S. patent application Ser. No. 12/253,831 entitled MEDICAL DEVICE FOR MODIFICATION OF LEFT ATRIAL APPENDAGE AND RELATED SYSTEMS AND METHODS, filed on Oct. 17, 2008, the disclosure of which is incorporated by reference herein in its entirety. Such anchoring systems or structures may be incorporated into embodiments of the present invention in conjunction with an associated tether and tissue growth member.

Figure 6:
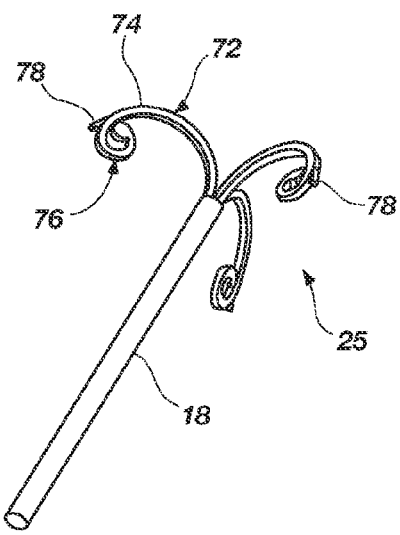
FIG. 6 is a perspective view of another embodiment of the anchoring member deployed from a distal end of a catheter, according to the present invention.

FIG. 6 depicts another embodiment of an anchoring member 25 which may be used in connection with the medical devices of the present invention. In this embodiment, the anchoring member 25 may include multiple j-shaped portions 72 extending radially outward to self expand from the distal portion of the catheter 18. Each j-shaped portion 72 includes a curved extension 74 and a distal coiled end 76. The periphery of each coiled end 76 may include one or more tapered nubs 78. In this manner, the coiled ends 76 of the j-shaped configuration can self expand and nest within the left atrial appendage and substantially anchor therein. Further, the spring-like quality of the curved extensions 74 allows for substantial pull on the tether to determine proper anchoring while substantially limiting any damage to the tissue within the left atrial appendage. It should be noted that it is not required that there by three j-shaped portions as is shown in the drawings. Rather, there may be more or additional j-shaped portions than shown as may be desired.

Figure 7A:
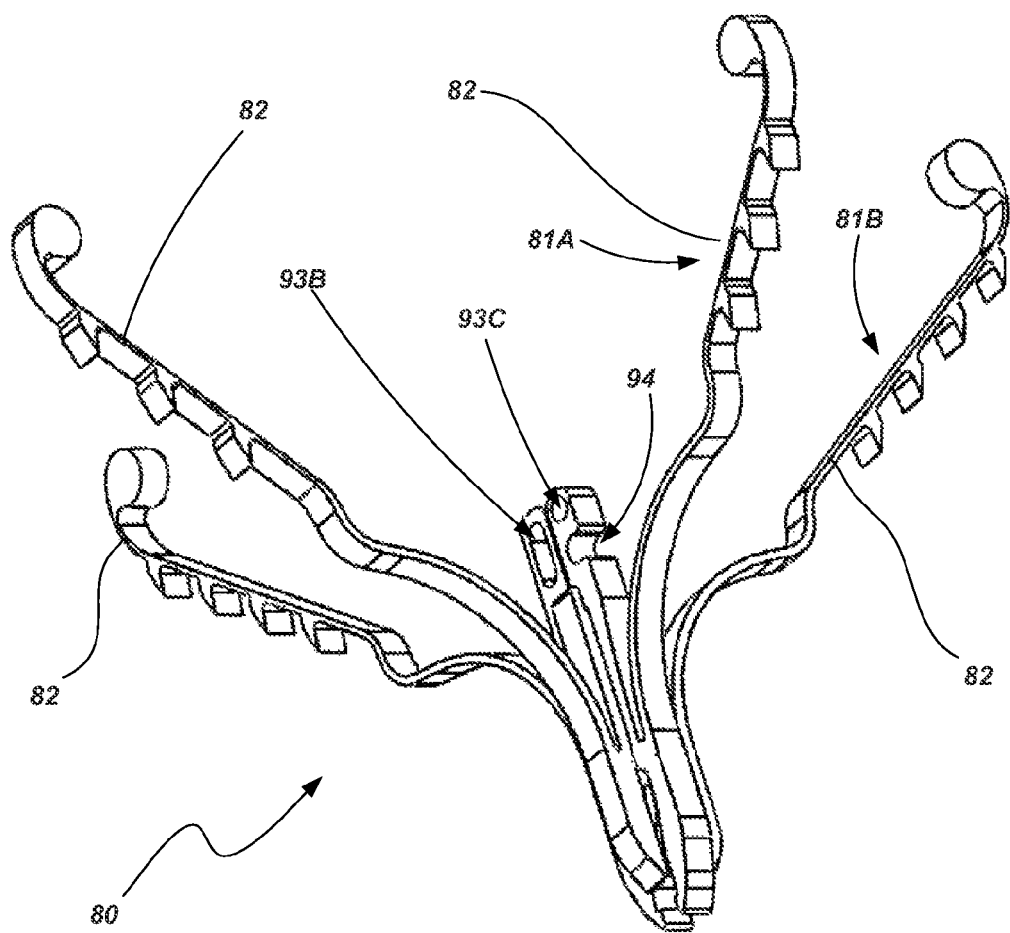

Referring now to FIGS. 7A-7E, another embodiment of an anchor is shown that may be used in accordance with one or more embodiments of the present invention. FIG. 7A shows a perspective view of the anchor 80, FIG. 7B shows a side view of the anchor 80, FIG. 7C shows a side view of the anchor 80 rotated approximately 90 degrees relative to that shown in FIG. 7B, and FIGS. 7D and 7E show side views of individual components used in forming the anchor 80. The anchor 80 may include multiple frame members 81A and 81B assembled together. While the frame members 81A and 81B may be substantially similar to one another, they are not necessarily identical to each other.

For example each frame member 81A and 81B may include one or more anchor legs 82 (in the present depicted embodiment, each frame member includes two anchor legs) with various features. The anchor legs 82 may include an arcuate distal end 83 having increased mass compared to the rest of the leg 82, the arcuate distal end 83 curving radially inwardly. Such arcuate distal ends act as atraumatic tips to help prevent potential puncture of the walls of the LAA when deploying the anchor 80. The inward curvature of the anchor legs distal ends are configured so that if the ends 83 are pushed against tissue within the LAA, the ends of the anchor legs 83 will roll radially inward. The anchor legs 82 may also include tissue engaging features 84 that are configured to press against and engage the trabeculated tissue wall of the LAA. The engaging features 84 may include, for example, proximally extending nubs, which may also be tapered. The engaging features 84 (as well as various tissue engaging features of other anchors and structures described herein) are configured to be atraumatic. For example, the engaging features 84 may engage with the tissue of an LAA by nestling amongst the trabeculations along the tissue wall.

The anchor legs 82 may further include a flare 85 or projection that extends or deviates radially outwardly relative to the remaining path of the anchor legs 82. The flare 85 assists in loading the anchor 80 into a catheter or other delivery mechanism such that when the flare engages the periphery of a catheter lumen, it causes the anchor legs 82 to deflect radially inwardly a sufficient distance to avoid the interference of the engaging features 84 with the inner wall of the catheter's lumen. It is also noted that the anchor legs 82 may exhibit different lengths than one another to further help facilitate placement of the anchor 80 within a catheter or other delivery mechanism. Thus, in one embodiment, each anchor leg 82 of a give anchor 80 may exhibit a different length than every other anchor leg.

The frame members 81A and 81B also include hub members 86A and 86B, respectively, that are cooperatively configured to effect mating or assembly of the frame members 81A and 81B to form the anchor 80. For example, referring specifically to FIGS. 7D and 7E, the hub 86A of one frame member 81A may include a slot 87 which may be accessed by displacing the free ends of two adjacent leg members 88A and 88B. The slot 87 may be sized and configured to accept, and mate with, a body portion 89 of hub member 86B from the other frame member 81B. The body portion 89 may have engagements surfaces 90A and 90B and be sized to fit snugly within the slot 87 of hub 86A. Other slots 91 and 92 within the hub members 86A and 86B may be used in facilitating assembly of the anchor members 81A and 81B.

The anchor members 81A and 81B may also include a plurality of through holes 93A, 93B and 93C and/or slots 94 or notches. These through holes 93A through 93C may be used for coupling of the tether 26 to the assembled anchor 80. For example, as shown in FIG. 7B, the tether 26 may pass through the various through holes 93A-93C, while also wrapping around the assembled hub members 86A and 86B to couple the tether 26 with the anchor 80 and to help maintain assembly to the frame members 81A and 81B. The tether may have a clip, a knot or otherwise be staked, as shown at 95, to keep the tether 26 from becoming unattached from the anchor 80.

In one embodiment, each frame member 81A and 81B may be formed as an integral, unitary and seamless component. For example, the frame members 81A and 81B may be formed by laser cutting from a sheet of material such as a nickel-titanium alloy. Thus, the anchor legs 82 of a given frame member 81A or 81B would lie in a common plane.

It is noted that the anchor 80, as well as other anchors described herein, are configured to be deployed deep within an atrial appendage. The ability to vary the relative position of an anchor with an associated tissue growth member (e.g., by varying the position of the two components along an associated tether) provides substantial flexibility in modifying an atrial appendage, particularly in light of the extreme variability from one atrial appendage to another.

Figure 8:
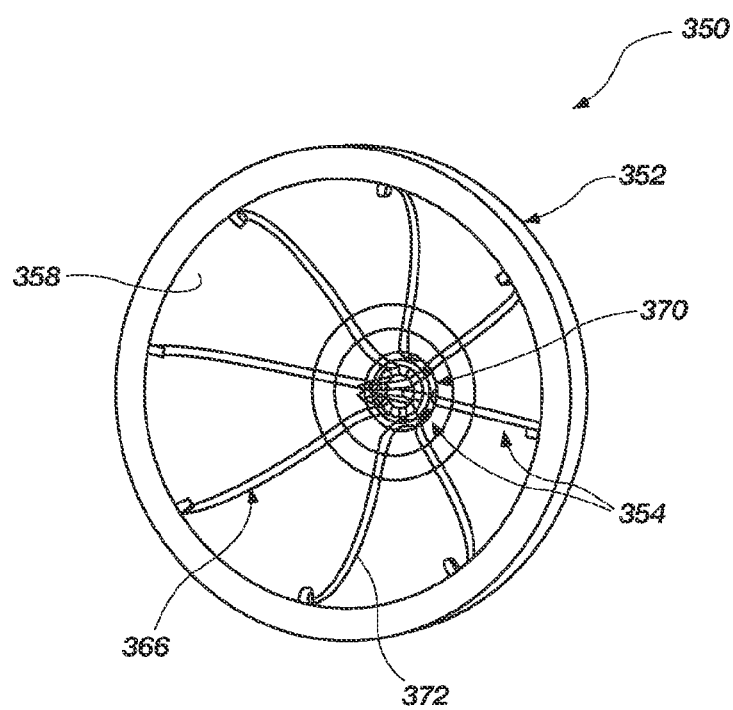
FIGS. 8 and 9 are perspective views of respective distal and proximal sides of an occluder, including a tissue growth member and a frame, that may be employed with the medical device system of FIGS. 1 and 1A, according to an embodiment of the present invention.
Figure 9:
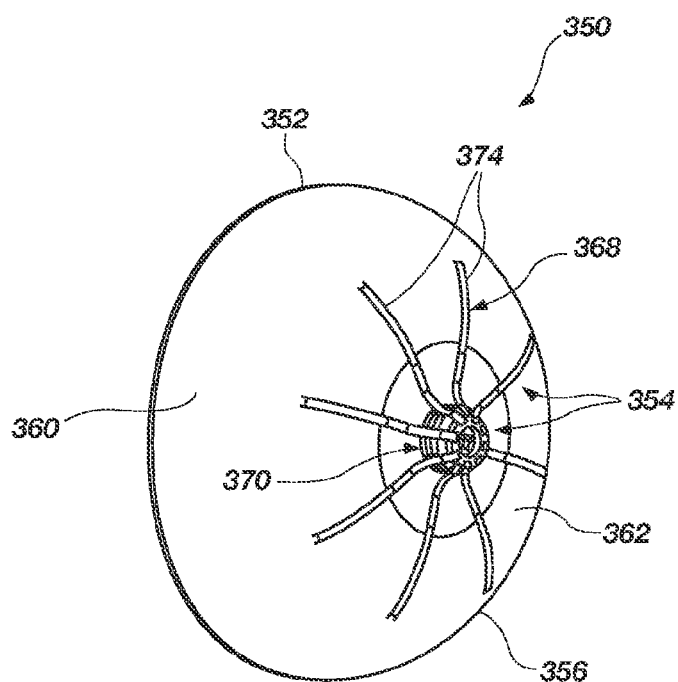

With respect to FIGS. 8 and 9, there is disclosed an embodiment of an occluder member 350, depicting perspective views of a distal side and a proximal side, respectively, of the occluder member 350. The occluder member 350 may be used in place of (or in some instances, in addition to) the tissue growth members 40 and associated support structure 42 described hereinabove.

The presently considered embodiment of the occluder member 350 may be employed with the medical device system depicted in FIG. 1 or FIG. 1A. The occluder member 350 includes a tissue growth member 352 and a frame 354. As with previously described embodiments, the tissue growth member 352 may include a porous member configured to promote tissue in-growth therein. The tissue growth member 352 may be a polymeric material, such as foam or other materials such as discussed above. In the embodiment shown in FIGS. 8 and 9, the tissue growth member 352 may exhibit a cup-like shape having an outer (or convex) surface 356 and an inner (or concave) surface 358, the outer surface 356 including a distal surface portion 360 and a proximal surface portion 362. The distal surface portion 360 of the tissue growth member 352 is sized and configured to be in direct contact with tissue within the LAA (such as shown with respect to tissue growth members 40a-40c in FIG. 4C).

The frame 354 or support structure of the occluder member 350 is configured to assist in expanding the tissue growth member 352 and to assist in collapsing the tissue growth member 352 for delivery through an associated catheter or other medical device. Such frame 354 may include an expander portion 366, a collapser portion 368 and a hub portion 370. The expander portion 366 may extend from the hub portion 370 with multiple expanding legs 372. In one embodiment, the legs 372 may extend along the inner surface 358 of the tissue growth member 352. The collapser portion 368 also may extend from the hub portion 370 with multiple collapsing legs 374. In one embodiment, the collapsing legs 374 may extend along the proximal surface portion 362 of the tissue growth member 352. With this arrangement, the collapser portion 368 of the frame 354 assists in collapsing the tissue growth member 352 (such as during a loading procedure) to a size wherein the occluder member 350 fits within the lumen of a catheter and may be displaced therethrough without damaging the tissue growth member 352. Further, when deploying the collapsed tissue growth member 352 from a catheter, the expander portion 366 of the frame 354 is configured to self expand to assist in opening the tissue growth member 352 so that much (if not all) of the distal surface portion 360 of the tissue growth member 352 is in direct contact with the tissue of the LAA.

Figure 10:
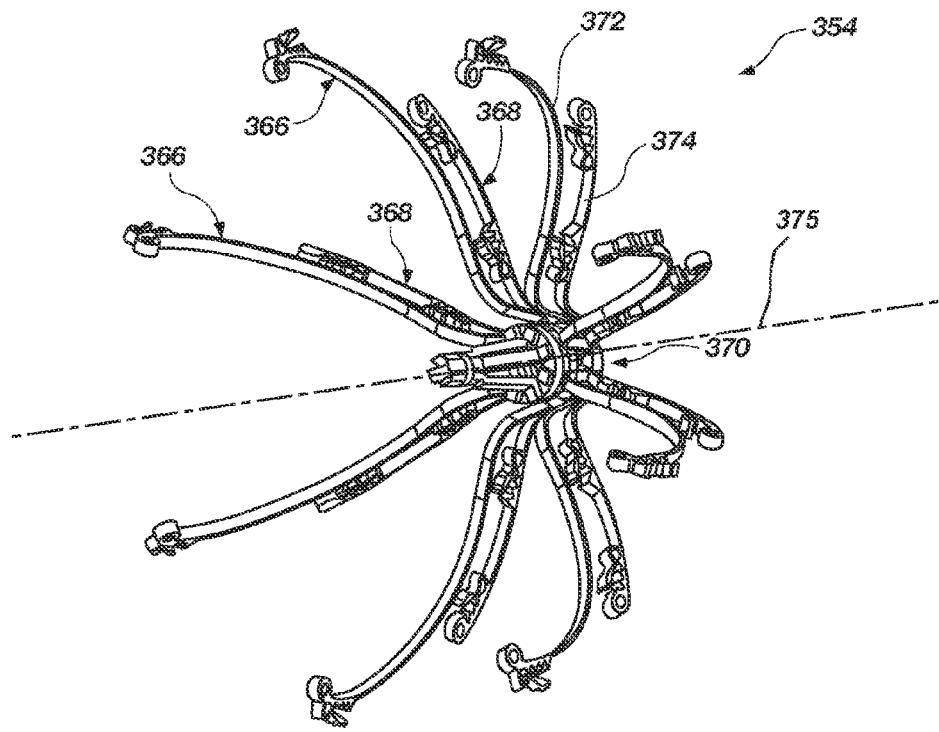
FIGS. 10 and 11 is a perspective view and a simplified side view of the frame of FIGS. 7 and 8, according to another embodiment of the present invention.
Figure 11:
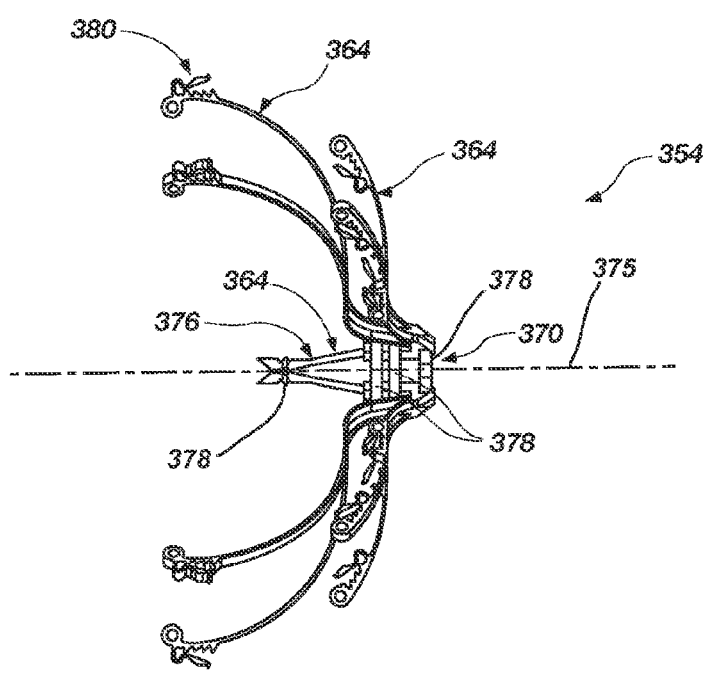

Referring now to FIGS. 10 and 11, FIG. 10 shows a perspective view and FIG. 11 shows a side view of the frame 354 previously described with respect to FIGS. 8 and 9. FIGS. 10 and 11 do not depict the tissue growth member 352 for purposes of clarity. Additionally, FIG. 10 is shown in a simplified form (i.e., some frame components are not shown) for purposes of clarity.

The frame 354 may include multiple discrete frame segments 364 that may be assembled with the hub portion 370 to collectively provide the frame 354. Each frame segment 364 includes a hub extension 376 with an expanding leg 372 and a collapsing leg 374 extending from a proximal end 376 of the hub extension 376.

Further, each frame segment 364 is configured to be substantially flat. Otherwise said, the hub extension 376, expanding leg 372 and collapsing leg 374 of a given frame segment 364 are substantially coplanar with respect to each other. In one embodiment, the frame segments 364 may each be laser cut or otherwise formed from a flat sheet of Nitinol, thereby, providing a substantially flat configuration to each of the frame segments 364. In this manner, the frame 354 (when assembled from the plurality of frame segments 364) may be configured to collapse within a catheter as well as self expand when deployed from a catheter with the frame segments 364 being deflected and displaced in the process.

Each frame segment 364 may be positioned radially and substantially symmetrical with respect to each other about a longitudinal axis 375 that extends through the hub portion 370. The frame segments 364 may be coupled with one or more rings 378 having notches on a radial inner surface, a radial outer surface or both to correspond with notches formed within the hub extension 376 of the frame segment. Due to each frame segment 364 being discrete with respect to the other frame segments 364, the expanding leg 372 and collapsing leg 374 may collapse or expand substantially independent from the other expanding and collapsing legs of the other frame segments 364. With this arrangement, when the tissue growth member 352 is deployed from a catheter, each of the frame segments 364 self expand, independent of each other, to facilitate the tissue growth member 352 to be in direct contact with the tissue of the LAA in a non-rigid and conformable manner. Further, the frame segments 364 each independently self expand so as to adapt to the varying anatomy that is encountered within the LAA.

Figure 12A:
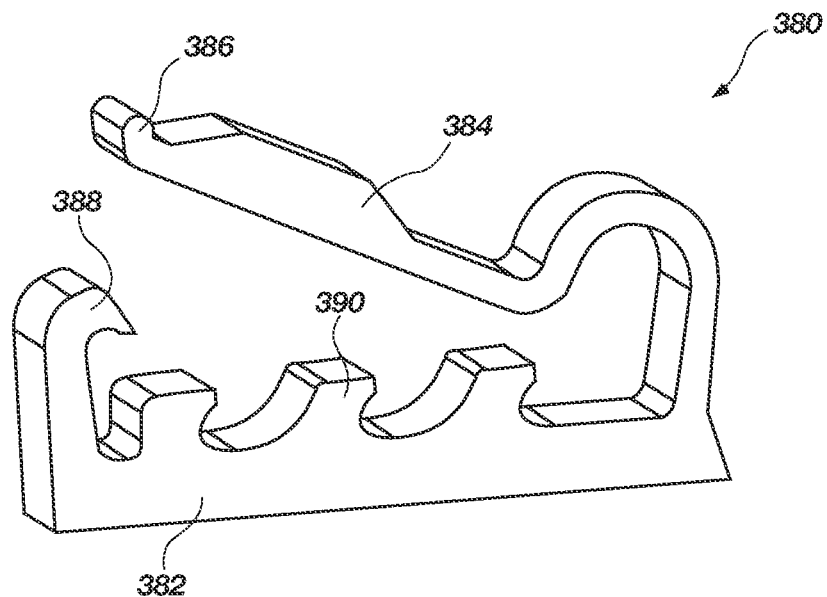
FIGS. 12A and 12B are perspective views of a clip in an open position and a closed position, respectively, formed in the frame depicted in FIGS. 10 and 11, according to another embodiment of the present invention.
Figure 12B:
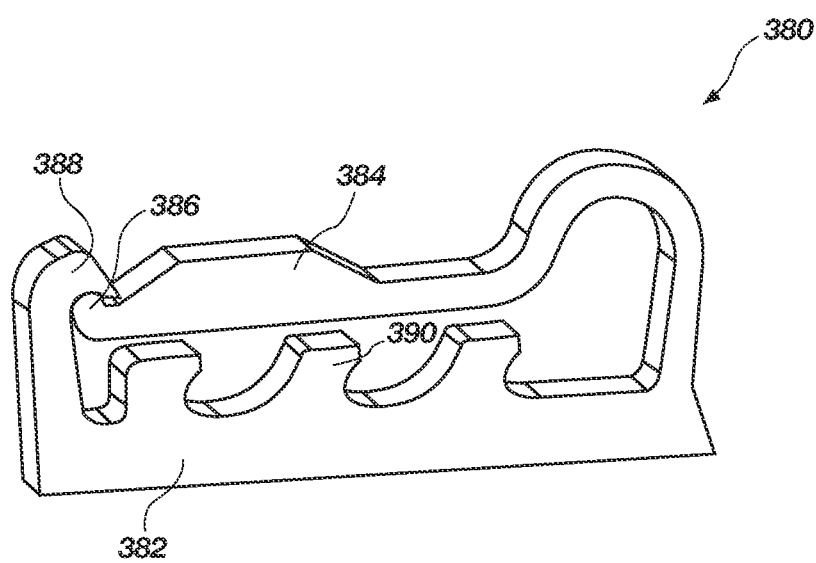

Each of the collapsing legs 374 and the expanding legs 372 may include one or more clips 380 formed therewith. FIGS. 12A and 12B are perspective enlarged views of clips 380 in an open and closed position, respectively, in accordance with an embodiment of the present invention. Such clips 380 may be formed in the proximal and/or distal portions of the legs for attaching the tissue growth member thereto (see FIGS. 8 and 9). The clips 380 may include a leg base portion 382, a cantilevered extension 384 with a free-end 386, and a pawl 388 that is configured to receive the free-end 386 of the cantilevered extension 384. Also, the clips 380 may include nubs 390 extending from the leg base portion 382 to provide traction or additional engagement with the tissue growth member 352. With the clips 380 formed in the collapsing and expanding legs of the frame, portions of the tissue growth member 352 are tucked between the cantilevered extension 384 and the leg base portion 382 and clipped to the legs by simply closing or pressing the free-end 386 against the pawl 388 until the free-end snaps under the pawl and is locked in position. As shown in FIGS. 10 and 11, the clips 382 may be integrally formed into the frame segments, such as by laser cutting. In other embodiments, other means of fastening the tissue growth member 352 to the frame 354 may be used (in lieu of, or in addition to the clips 380) including, for example, adhesives, sutures, or other mechanical structures or devices.

Figure 13:
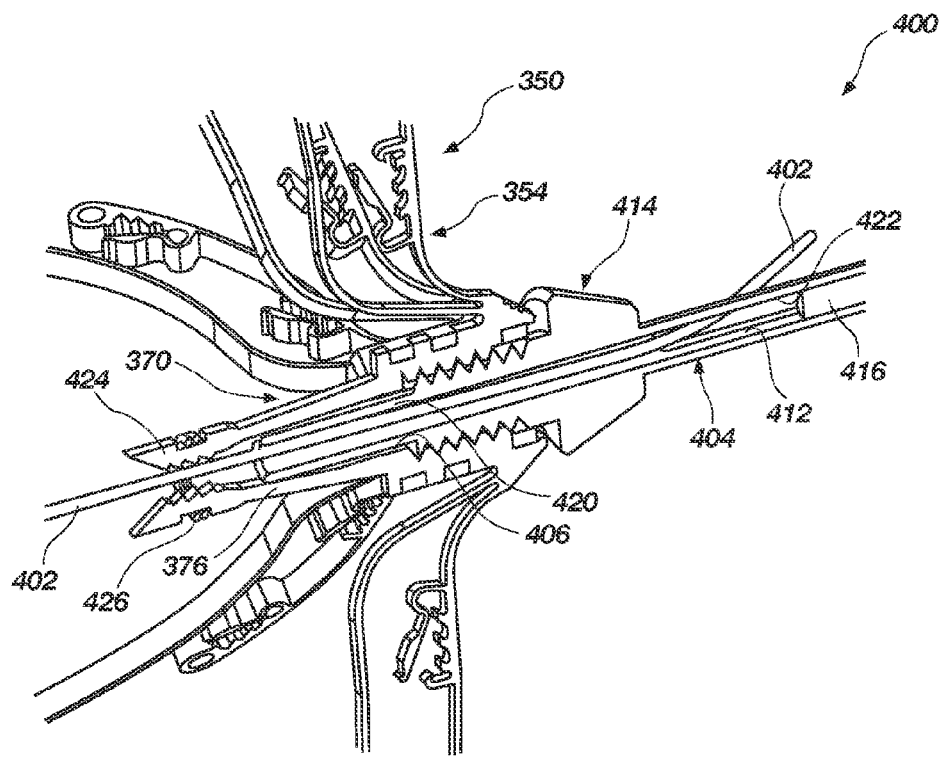
FIGS. 13 and 14 are simplified perspective views of a hub in an open and closed position, respectively, taken along a center line of the frame depicted in FIG. 10, depicting a portion of a medical device system, according to another embodiment of the present invention.
Figure 14:
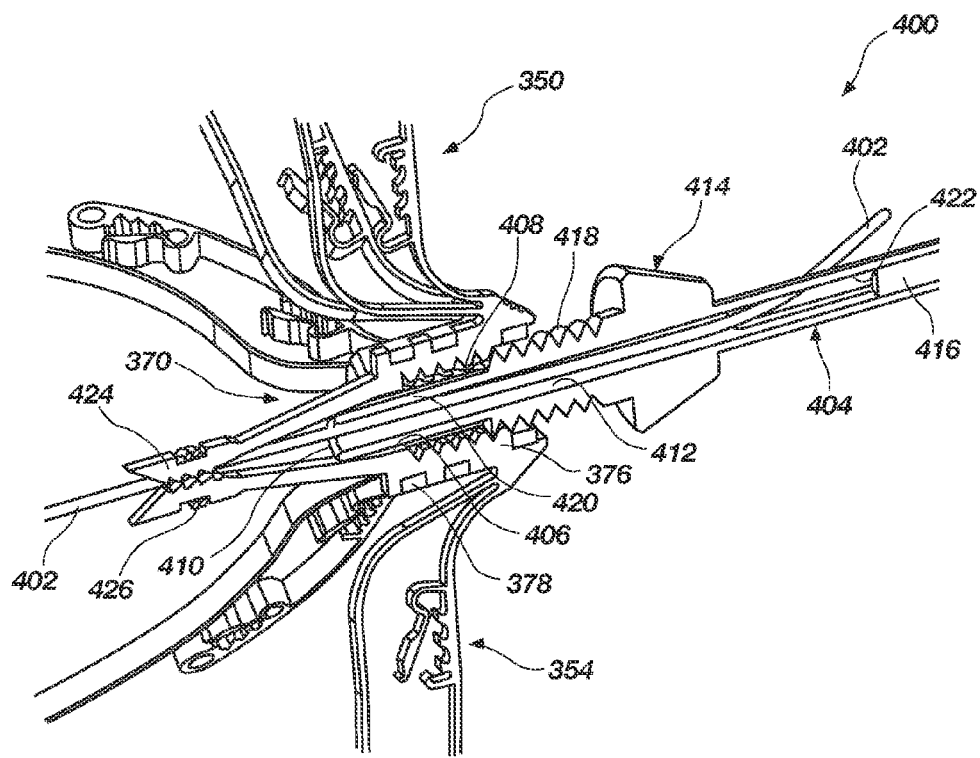
Figure 15A:
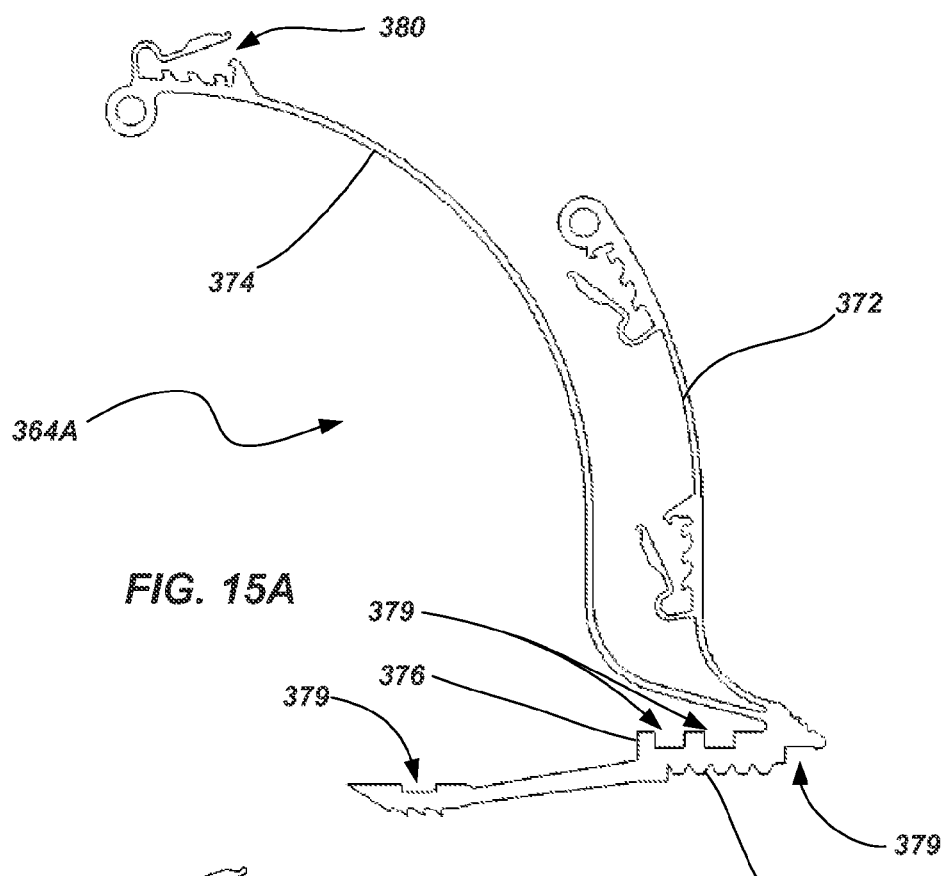
FIGS. 15A and 15B are side views of components that may be used in a frame for an occluder in accordance with various embodiments of the present invention.
Figure 15B:
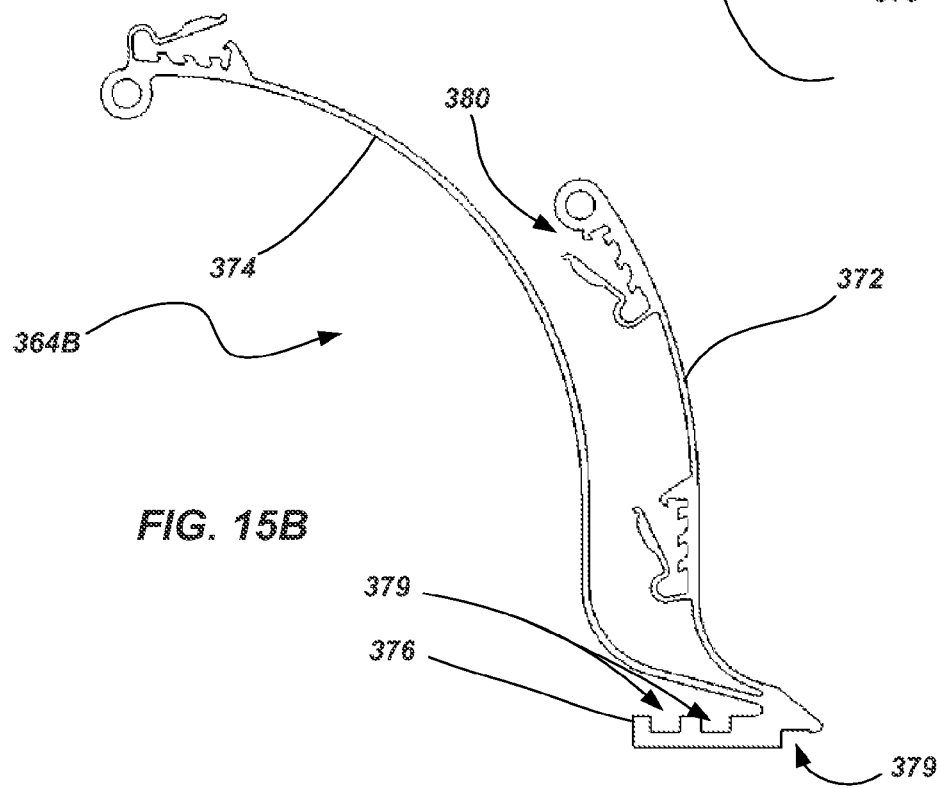

Referring now to FIGS. 13 and 14, a simplified side view of portions of a medical device system 400 in an open position (also referred to as an expanded or deployed position) and a closed position (also referred to as a contracted position), according to one embodiment, is depicted. The medical device system 400 may include the occluder member 350, a tether filament 402 and a pusher member 404. It is noted that, for purposes of clarity, a tissue growth member is not shown in FIGS. 13 and 14, although one is contemplated and those of ordinary skill in the art will recognize its use an implementation in the following description. Additional reference is made during the following description to FIGS. 15A and 15B which show side views of frame segments 364A and 364B. It is noted that the frame 354 of the occluder member 350 may be formed of a plurality of frame segments 364A and 364B. In one embodiment, the frame of the occluder member 350 may include four of each type of frame segments 364A and 364B which alternate in their positions (i.e., each frame segment 364A is adjacent to two frame segments 364B and vice versa). As set forth above, the frame segments 364A and 364B may include expanding legs 374, collapsing legs 372 and hub extensions 376 that have inner and outer notches 379 for engaging ring members during assembly of the frame. As previously noted, such frame segments 364A and 364B may be formed, for example by laser cutting from a flat sheet of desired material such as a nickel-titanium alloy (e.g., Nitinol). Such a configuration provides for the expanding leg 374, collapsing leg 372 and hub extension 376 to be coplanar.

Additional detail regarding the function and structure of a hub portion 370 of the occluder member 350, as facilitated with the tether filament 402 and the pusher member 404, is now set forth in accordance with one embodiment of the invention. The hub portion 370 may define a hole 406 extending centrally therethrough and may further include a shoulder portion 408 that at least partially defines the hole 406. As previously set forth, the hub portion 370 is defined via the assembled multiple hub extensions 376 radially oriented and positioned with the one or more rings 378. The hub portion of the frame 354 enables the occluder member 350 to slide over the tether filament 402, such as previously depicted in the embodiments described in FIGS. 3A-3D and 4A-4C.

The pusher member 404 includes a distal end 410 and a proximal end (not shown) with a lumen 412 extending longitudinally through at least a portion of the pusher member 404. The pusher member 404 includes a coupling member 414 at or proximate the distal end 410 of the pusher member 404 and a cutter 416 disposed within the lumen 412, a distal end of the cutter 416 being proximal or adjacent to an outlet 422 defined in a wall of the pusher member 404. The coupling member 414 may include a threaded portion 418 and a non-threaded distal extension 420, the extension 420 extending distal of the threaded portion 418.

As depicted in FIG. 13, when the threaded portion 418 is fully engaged within the hole 406 defined in the hub portion 370, the non-threaded distal extension 420 engages the hub extensions 376 and places a gripper portion 424 of the hub portion 370 in an open position. In this manner, the occluder member 350 may slide or move over the tether filament 402, through a catheter while in a collapsed position as well as once deployed from the catheter, with the tether filament 402 extending through at least the coupling portion 414 or a distal portion of the pusher member 404 and exiting from the pusher member 404 through the outlet 422 defined in the wall of the pusher member 404.

With respect to FIG. 14, once the occluder member 350 is positioned as desired such that the tissue growth member (not shown) is in direct contact with tissue in the LAA, the pusher member 404 may be un-threaded or removed from the occluder member 350, thereby causing the gripper portion 424 of the hub portion 370 to engage or grip the tether filament 402. That is, as the pusher member 404 is un-threaded, the distal extension 420 is moved proximally which causes the gripper portion 424 to move to the radially inward position (i.e., the radially closed position) to grip onto the tether filament 402 that is anchored distally and deep within a lobe of the LAA. In one embodiment, the gripper portion 424 may include bands 426 disposed around the gripper portion 424 to bias the gripper portion in the closed state and assist in more effectively gripping the tether filament 402. In other embodiments, the hub extensions may be configured to be biased towards the closed position even without the aid of other biasing elements. This configuration enables the hubs to work as a locking element to maintain the occluder member 350 in a desired position relative to the tether (and, thus, relative to an associated anchor).

The pusher member 404 can then be fully removed from the hub portion 370 of the occluder member 350 and, if the physician is satisfied with the position of the occluder member, the cutter element 416 can be moved distally to slice the tether filament 402. Alternatively, depending on the anatomy of the LAA, another occluder member may be loaded in a catheter and slid over the tether filament 402 to position within the LAA.

Figure 16:
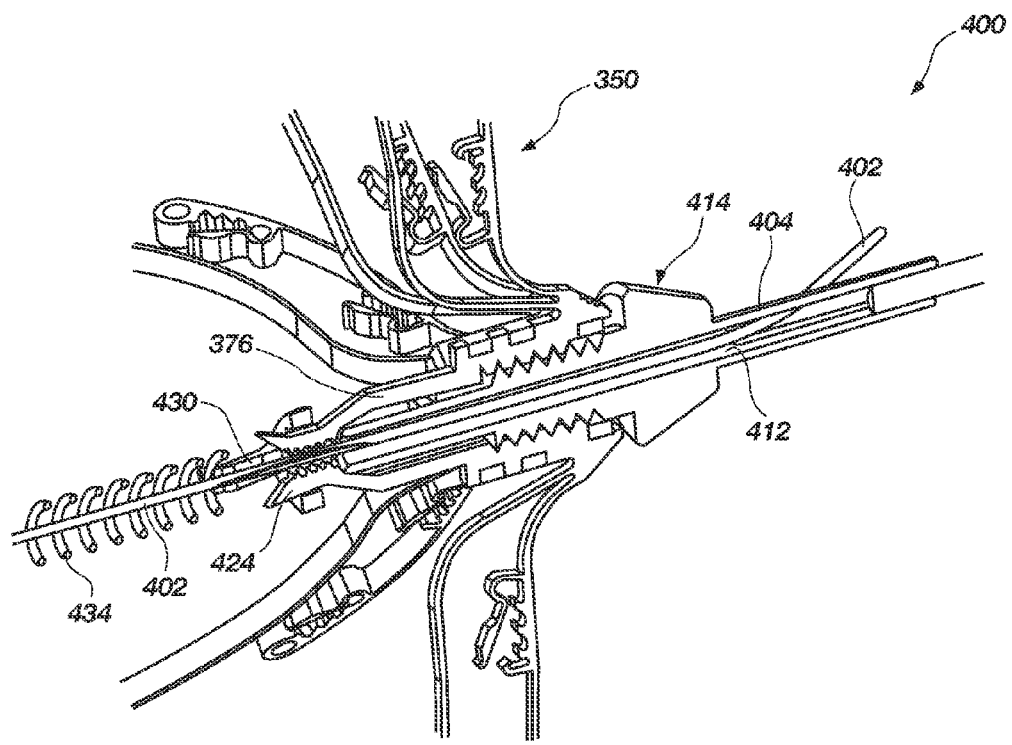
FIG. 16 is a simplified perspective view of the frame, depicting a portion of a medical device system taken along a center line, according to another embodiment of the present invention.
Figure 17:
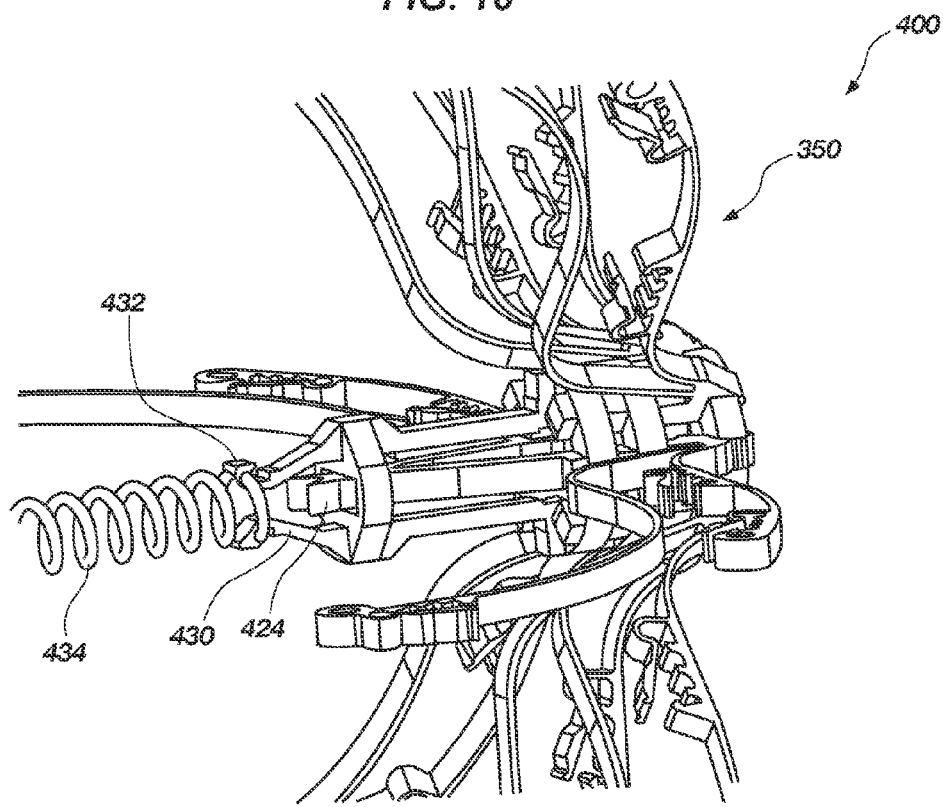
FIG. 17 is a perspective view of a portion of the frame of FIG. 16, according to the present invention.

With reference to FIGS. 16 and 17, another embodiment of a portion of the medical device system 400 is depicted. This embodiment is similar to the embodiment described with respect to FIGS. 14 and 15, except in this embodiment, the hub extensions 376 may include a guide portion 430 that may be associated with the gripper portion 424. Further, at the distal end of the guide portion 430, there is a pawl 432 to latch a tether guide coil 434. The tether guide coil 434 extends distally and the tether filament 402 extends axially through the tether guide coil 434. The tether guide coil 434 extends a length sufficient to substantially prevent the tissue growth member (not shown) from contacting the tether filament 402 while the occluder 350 is in a collapsed position and being pushed distally within a catheter.

It is also contemplated that the pusher member 404 may include a coil (not shown) that is positioned proximal to the coupling member 414 and over the pusher member 404 such that the coil and the lumen 412 of the pusher member 404 have a common axis. Further, it is also contemplated that the occluder 350, the pusher member 404 and the tether filament 402 may include radiopaque characteristics or markers so that the relevant portions of the medical device system 400 can be viewed with imaging techniques known in the art.

Figure 18:
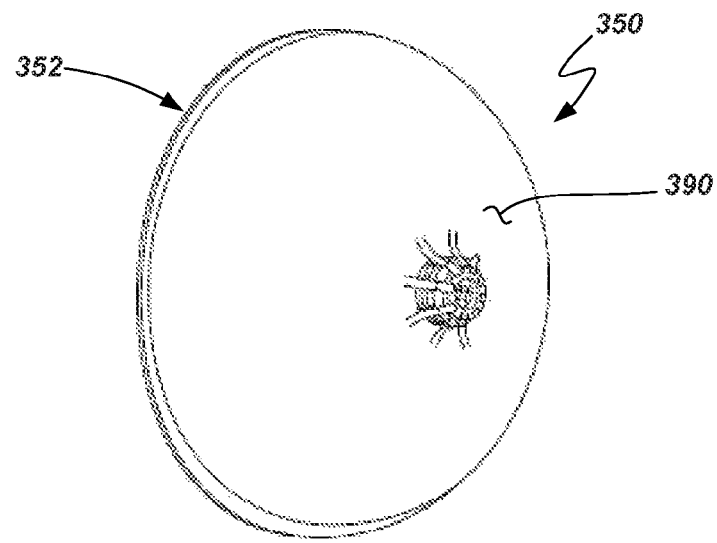
FIG. 18 is a perspective view of the proximal side of an occluder in accordance with another embodiment of the present invention.
Figure 19:
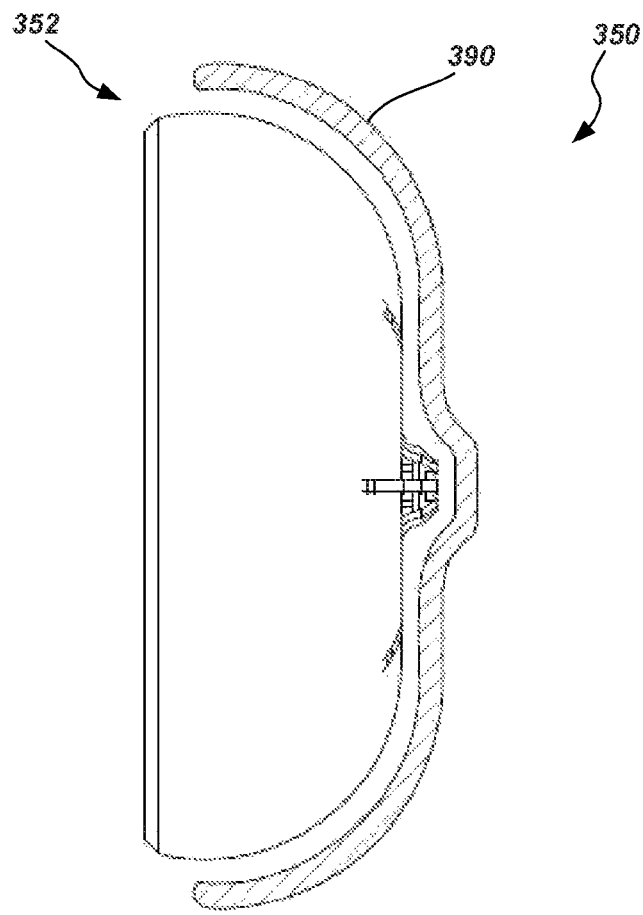
FIG. 19 is a partial cross-sectional side view of the occluder shown in FIG. 18.

Referring now to FIGS. 18 and 19, an occluder 350 is shown in accordance with another embodiment of the present invention. FIG. 18 shows a front perspective view while FIG. 19 shows a side, partial cross-sectional view of the occluder 350. The occluder 350 is similar to the embodiments show and described with respect to FIGS. 7 and 8, but also includes an additional material layer 390 associated with the tissue growth member 352. FIG. 19 shows the additional material layer 390 in an "exploded" state for purposes of illustration. However, the additional material layer 390 is, in actuality, contiguous with the underlying foam or other material forming the tissue growth member 352, the additional material layer 390 being attached thereto by, for example, an adhesive. The additional material layer 390 may include a polytetrafluoroethylene (PTFE) or expanded PTFE (ePTFE). Such a surface provides a smooth surface on the proximal side of the tissue growth member to tailor the tissue growth pattern once the occluder is deployed within an atrial appendage. It is noted the additional material layer 390 may be configured to allow a portion of the frame to be exposed on the proximal side (e.g., the hub portion) such as shown in FIG. 18, or it may be configured to cover substantially all of the frame along the proximal side such as is shown in FIG. 19.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes all modifications, equivalents, and alternatives falling within the spirit and scope of the invention as defined by the following appended claims.

What is claimed is:

1. A method for modifying a left atrial appendage, comprising:
   positioning a catheter adjacent the left atrial appendage;
   anchoring a tether within the left atrial appendage;
   sliding at least one tissue growth member over the tether with a pusher member having threads such that the pusher member is rotatably coupled to a hub of the tissue growth member;
   deploying the at least one tissue growth member within the left atrial appendage; and
   maintaining the at least one tissue growth member in the left atrial appendage with a locking element, the locking element including multiple fingers that collapse directly dependent upon proximally moving the pusher member relative to the tissue growth member.

2. The method according to claim 1, wherein anchoring a tether further comprises:
   positioning the catheter having an anchoring member in a constrained configuration within the catheter relative to the left atrial appendage; and
   deploying the anchoring member in an expanded configuration to anchor the anchoring member in the left atrial appendage.

3. The method according to claim 1, wherein the sliding the at least one tissue growth member over the tether comprises sliding a plurality of tissue growth members over the tether and within the left atrial appendage.

4. The method according to claim 1, further comprising selectively choosing the at least one tissue growth member from a variety of differently configured tissue growth members to slide over the tether.

5. The method according to claim 4, further comprising obtaining imaging information regarding the left atrial appendage and wherein selectively choosing is based, at least in part, on the obtained imaging information.

6. The method according to claim 1, further comprising selectively choosing a specific number of tissue growth members for sliding within the left atrial appendage.

7. The method according to claim 1, further comprising selectively choosing a specific size from a plurality of tissue growth members for placing within the left atrial appendage.

8. The method according to claim 1, wherein sliding at least one tissue growth member over the tether further comprises positioning the catheter within the left atrial appendage and deploying the tissue growth member from the catheter while slidably coupled with the tether.

9. The method according to claim 1, wherein the sliding at least one tissue growth member over the tether further comprises sliding an expandable porous tissue growth member over the tether.

10. The method according to claim 1, wherein the sliding at least one tissue growth member over the tether further comprises pushing the at least one tissue growth member over the tether with the pusher member.

11. The method according to claim 1, further comprising loading the at least one tissue growth member into the lumen of a catheter in a constrained state prior to deploying the at least one tissue growth member in the left atrial appendage.

12. The method according to claim 1, wherein deploying the at least one tissue growth member within the left atrial appendage includes deploying the at least one tissue growth member within a first lobe of the lest atrial appendage and wherein the method further comprises deploying at least one other tissue growth member in a second lobe of the left atrial appendage.

13. The method according to claim 1, wherein the maintaining comprises collapsing the multiple fingers with a hand wrapped around the multiple fingers.

14. A method for modifying a left atrial appendage, comprising:
   positioning a catheter adjacent the left atrial appendage;
   pushing a medical device having tines through a lumen of the catheter;
   anchoring the medical device to the left atrial appendage with the tines;
   deploying a tissue growth member of the medical device from the catheter with a pusher member having threads rotatably coupled to the medical device;
   collapsing multiple fingers of a locking element directly dependent upon proximally displacing the pusher member relative to the tissue growth member; and
   disengaging the pusher member from the medical device.

15. The method according to claim 14, wherein, the disengaging comprises cutting a tether with a cutting element, the tether extending between the tines of the medical device and the tissue growth member of the medical device.

16. The method according to claim 15, wherein the disengaging comprises collapsing the multiple fingers of the locking element over the tether.

17. The method according to claim 14, wherein the disengaging comprises proximally moving the pusher member from a hub of the medical device by rotating a threaded coupling member from the hub of the medical device.

18. The method according to claim 14, wherein the deploying comprises maintaining the multiple fingers of the locking element in a non-collapsed position with a distal portion of the pusher member engaged with a hub of the medical device.

19. The method according to claim 14, wherein the disengaging comprises removing the pusher member from a hub of the medical device.

20. The method according to claim 14, wherein the collapsing comprises collapsing with a band wrapped around the multiple fingers.

* * * * *